US008664292B2

(12) United States Patent
Pavlin

(10) Patent No.: US 8,664,292 B2
(45) Date of Patent: Mar. 4, 2014

(54) COMPOSITIONS AND ARTICLES CONTAINING A CROSS-LINKED POLYMER MATRIX AND AN IMMOBILIZED ACTIVE LIQUID, AS WELL AS METHODS OF MAKING AND USING THE SAME

(75) Inventor: Mark S. Pavlin, Savannah, GA (US)

(73) Assignee: Croda International PLC (GB)

(*) Notice: Subject to any disclaimer, the term of this patent is extended or adjusted under 35 U.S.C. 154(b) by 1021 days.

(21) Appl. No.: 11/945,184

(22) Filed: Nov. 26, 2007

(65) Prior Publication Data

US 2008/0070025 A1 Mar. 20, 2008

Related U.S. Application Data

(63) Continuation-in-part of application No. 11/140,160, filed on May 27, 2005, now abandoned.

(60) Provisional application No. 60/870,822, filed on Dec. 19, 2006, provisional application No. 60/574,759, filed on May 27, 2004, provisional application No. 60/618,449, filed on Oct. 13, 2004.

(51) Int. Cl.
*A61L 9/01* (2006.01)

(52) U.S. Cl.
USPC .......................................................... 523/102

(58) Field of Classification Search
USPC .......................................................... 523/102
See application file for complete search history.

(56) References Cited

U.S. PATENT DOCUMENTS

| | | | | |
|---|---|---|---|---|
| 4,328,322 A * | 5/1982 | Baron | | 521/163 |
| 4,389,513 A | 6/1983 | Miyazaki | | |
| 4,590,111 A * | 5/1986 | Takeuchi | | 428/67 |
| 4,767,812 A * | 8/1988 | Chapin et al. | | 524/144 |
| 4,873,307 A * | 10/1989 | Federici et al. | | 528/60 |
| 4,876,290 A | 10/1989 | Vivant | | |
| 5,008,115 A | 4/1991 | Lee et al. | | |
| 5,104,930 A * | 4/1992 | Rinde et al. | | 524/871 |
| 5,162,481 A * | 11/1992 | Reid et al. | | 528/48 |
| 5,780,527 A * | 7/1998 | O'Leary | | 523/102 |
| 5,881,648 A * | 3/1999 | Pavlin | | 101/491 |
| 6,111,655 A | 8/2000 | Kashihara et al. | | |
| 6,359,031 B1 | 3/2002 | Lykke et al. | | |
| 6,375,966 B1 * | 4/2002 | Maleeny et al. | | 424/405 |
| 6,399,713 B1 | 6/2002 | MacQueen et al. | | |
| 6,401,724 B1 * | 6/2002 | Sawyer | | 132/200 |
| 6,403,063 B1 * | 6/2002 | Sawyer | | 424/61 |
| 6,503,577 B2 | 1/2003 | Keller | | |
| 6,783,821 B2 * | 8/2004 | Ries et al. | | 428/34.1 |
| 6,846,491 B1 * | 1/2005 | Richards | | 424/405 |
| 6,870,011 B2 | 3/2005 | MacQueen et al. | | |
| 2001/0005744 A1 * | 6/2001 | Shelvey | | 528/59 |
| 2002/0068811 A1 | 6/2002 | Orth et al. | | |
| 2002/0127266 A1 | 9/2002 | Sawhney et al. | | |
| 2002/0128421 A1 * | 9/2002 | Shelvey | | 528/58 |
| 2002/0147053 A1 * | 10/2002 | Chrisman, III | | 473/125 |
| 2003/0065084 A1 | 4/2003 | MacQueen et al. | | |
| 2003/0105221 A1 * | 6/2003 | Christenson et al. | | 524/589 |
| 2003/0110682 A1 | 6/2003 | Williams et al. | | |
| 2003/0113354 A1 | 6/2003 | Schmid et al. | | |
| 2003/0165692 A1 | 9/2003 | Koch et al. | | |
| 2003/0195293 A1 | 10/2003 | Lubnin et al. | | |
| 2003/0220464 A1 | 11/2003 | Wu et al. | | |
| 2004/0137031 A1 * | 7/2004 | Seitz et al. | | 424/408 |
| 2004/0220377 A1 | 11/2004 | Kuntimaddi et al. | | |
| 2005/0267231 A1 * | 12/2005 | Pavlin | | 523/102 |
| 2005/0271735 A1 * | 12/2005 | Stover et al. | | 424/490 |
| 2006/0120913 A1 | 6/2006 | Wuest | | |
| 2006/0252848 A1 | 11/2006 | Guillaume | | |
| 2008/0022464 A1 * | 1/2008 | Lambert et al. | | 8/115.51 |
| 2008/0070025 A1 * | 3/2008 | Pavlin | | 428/304.4 |
| 2011/0071064 A1 * | 3/2011 | Lei et al. | | 510/119 |
| 2011/0117156 A1 * | 5/2011 | Lin et al. | | 424/409 |

FOREIGN PATENT DOCUMENTS

| | | |
|---|---|---|
| CN | 1134115 | 10/1996 |
| EP | 1099474 A1 | 5/2001 |
| EP | 1443068 A1 | 8/2004 |
| FR | 2 695 033 | 3/1994 |
| JP | 61-148116 | 7/1986 |
| JP | 62-084127 | 4/1987 |
| JP | 03-258899 | 11/1991 |
| JP | 04-353515 | 12/1992 |
| JP | 07/145299 | 6/1995 |
| WO | 02/094329 A1 | 11/2002 |
| WO | 02/094900 A1 | 11/2002 |
| WO | 03/097218 A1 | 11/2003 |
| WO | 2005/118008 A2 | 12/2005 |

OTHER PUBLICATIONS

Extended European Search Report, EP 07872360.8, mailed Dec. 23, 2010, 6 pages.
International Search Report and Written Opinion, PCT/US2011/061349, mailed Apr. 11, 2012, 10 pages.
English translation of Office Action for Japanese Application No. 2007-515344, mailed Mar. 19, 2012, 4 pages.

* cited by examiner

*Primary Examiner* — Liam Heincer
*Assistant Examiner* — Michael A Salvitti
(74) *Attorney, Agent, or Firm* — Meunier Carlin & Curfman, LLC

(57) ABSTRACT

The invention relates to compositions and articles containing a cross-linked polymer matrix and an immobilized active liquid, as well as methods of making and using the same.

27 Claims, No Drawings

COMPOSITIONS AND ARTICLES CONTAINING A CROSS-LINKED POLYMER MATRIX AND AN IMMOBILIZED ACTIVE LIQUID, AS WELL AS METHODS OF MAKING AND USING THE SAME

RELATED APPLICATION DATA

This application claims priority of U.S. Provisional Patent Application No. 60/870,822, filed Dec. 19, 2006, and is a also continuation-in-part of U.S. patent application Ser. No. 11/140,160 now abandoned, which claimed priority of U.S. Provisional Patent Application Nos. 60/574,759, filed May 27, 2004, and 60/618,449, Oct. 13, 2004.

BACKGROUND OF THE INVENTION

1. Field of the Invention

The invention relates to compositions and articles containing a polymer matrix and an immobilized active liquid therein, as well as methods of making and using the same.

2. Description of the Related Art

The curing and/or cross-linking of polymeric systems, for example epoxy systems, is described in textbooks and industrial handbooks such as "Handbook Of Epoxy Resins" by Henry Lee and Kris Neville (McGraw Hill, 1967), "The Epoxy Formulators Manual" by the Society of Plastics Industry, Inc. (1984), and the Encyclopedia of Science and Technology (Kirk-Othmer, John Wiley & Sons, 1994). Until recently, curing such systems and others related thereto in a manner capable of immobilizing active liquids, such as those having and/or containing fragrance, has been very difficult, especially when durability and performance under a dynamic range of operation conditions are required from such systems.

For example, JP 032558899A requires the use of a solid powder system, while JP07145299 requires the use of a pre-formed urethane-containing epoxy resin cross-linked in the absence of a polyamine and/or an active liquid containing a perfume. Further, the above-mentioned JP references refer specifically and only to fragranced articles, such as air fresheners. Because of this narrow goal to make such articles, the reaction and reaction products described therein fail to have a dynamic range of performance capabilities. Moreover, they fail to provide a product that is durable in the absence of a support. Therefore, a need arises for controllable reaction conditions that yield dynamic reaction products containing durable matrices capable of immobilizing any and/or all types of active liquids therein.

Compositions such as fragrance objects, even more specifically air fresheners, are well known devices that release a fragrance into the air of a room of a house, area of a public building (e.g. a lavatory) or the interior of a car to render the air in that area more pleasing to the occupant. Only substantially non-aqueous gels, for example the thermoplastic polyamide-based products described in U.S. Pat. Nos. 6,111,655 and 6,503,577 and the thermo-set poly(amide-acid)s of U.S. Pat. No. 5,780,527 and of U.S. Pat. No. 6,846,491, are homogeneous, transparent solids that can be easily charged, when in liquid form, to a mold and thus made into a visually attractive solid shape without the use of a means of support. However, during preparation of thermoplastic gels, the components must be heated to a temperature above the gelation temperature of the mixture, a process detrimental to the volatile and sometimes temperature sensitive active liquid such as fragrance, pesticide or surfactant. During storage or use, these gels must not be exposed to low temperatures because they can turn unattractively cloudy. Furthermore, these gels must not be exposed to high temperatures because they will turn liquid, losing their shape or leaking from their container. These drawbacks are serious for air fresheners necessarily exposed to a dynamic range of temperatures, such as car interior fresheners. The latter are often exposed to low temperatures in winter and temperatures in excess of 110° F. on summer days when the car is parked in direct sunlight. In addition, thermoplastic gels are soft solids that are easily deformed if scraped, dropped, poked, or wiped. Thus, these conventional gels do not provide compositions and/or articles that are readily durable and capable of operating at a wide range of operating parameters.

SUMMARY OF THE INVENTION

The present inventor has discovered a more efficient solution to providing thermo-set, i.e. cross-linked, polymeric matrices containing immobilized active liquids homogeneously distributed throughout that are durable and stable over a wide range of use conditions.

One object of the present invention is the reaction product obtained simply by mixing a compound having at least one, and preferably at least two functional groups selected from the group consisting of epoxy, isocyanate, anhydride, and acrylate with a polyamine in the presence of an effective amount of an active liquid.

Other objects of the present invention are compositions comprising the reaction product obtained by mixing a compound having at least one, preferably two or more functional groups selected from the group consisting of epoxy, isocyanate, anhydride, and acrylate with a polyamine in the presence of an effective amount of an active liquid and articles containing this reaction product. As non-limiting examples, such article may be an air freshener, laundry fragrance sheet, laundry fabric softener sheet, laundry anti-static sheet, storage fragrance article, a pharmaceutical distribution article, a neutraceutical distribution article, a bioceutical distribution article, a moldicide distribution article, a bactericide distribution article, a pesticide distribution, a decorative article, a biomedical sensor and/or an analytical device. Methods of making such the above-mentioned reaction products, compositions, and/or articles are a further object of the invention.

One aspect of the invention optionally relates to embodiments when the cured polymeric matrix is a reaction product of a compound having at least two functional groups selected from the group of epoxy, isocyanate, anhydride, and acrylate with a polyamine in the presence of an active liquid and a reaction rate modifier, either an accelerant (i.e. a catalyst) or a retardant. Further embodiments include method of making and using such compositions and articles.

Another object of the present invention is a composition and/or article containing a cured polymeric matrix and an active liquid where the active liquid is uniformly immobilized within the cured polymeric matrix and the cured polymeric matrix is a reaction product of mixing a compound having at least two non-aromatic isocyanate functional groups. Further embodiments include method of making and using such compositions and articles.

Another object of the present invention is a composition and/or article containing a cured polymeric matrix and an active liquid where the active liquid is immobilized uniformly within the cured polymeric matrix and the cured polymeric matrix is a reaction product of mixing a compound having at least one but preferably more than one isocyanate functional group and the polyamine is a polymer terminated by the residue from an aminobenzoic acid molecule. Further embodiments include method of making and using such compositions and articles.

Another object of the present invention is a composition and/or article containing a cured polymeric matrix and an active liquid where the active liquid is immobilized within the cured polymeric matrix and the cured polymeric matrix is a reaction product of a liquid containing compounds having at least two functional groups selected from the group of epoxy, isocyanate, anhydride, and acrylate with a liquid containing a polyamine in the presence of an active liquid and water. Further embodiments include method of making and using such compositions and articles.

Another object of the present invention is a composition and/or article containing a cured polymeric matrix and an active liquid where the active liquid is immobilized within the cured polymeric matrix and the cured polymeric matrix is a reaction product of mixing a liquid containing compounds having two or more isocyanate functional groups with a polymeric polyamine in the presence of an active liquid where the polymeric polyamine has an amine number of from 1 to 100 meq KOH/g and has a viscosity, measured at 150° C., of no greater than about 500 cP. Further embodiments include method of making and using such compositions and articles.

Another object of the present invention is a composition and/or article containing a cured polymeric matrix and an active liquid where the active liquid is immobilized within the cured polymeric matrix and the cured polymeric matrix is a reaction product of mixing a liquid containing compounds having at least two functional group selected from an epoxy, an isocyanate, an anhydride, and an acrylate with a polyamine in the presence of an active liquid or water or mixtures thereof; and where the polyamine is a liquid at room temperature. Further embodiments include method of making and using such compositions and articles.

It is accordingly an additional object of the invention to provide a method for preparing transparent, flexible, and stable solids useful in air care, therapeutic, pesticidal, nutritional, surface treating and other products by immobilizing active liquids uniformly in a polymeric matrix via the reaction of a liquid polyepoxy or polyisocyanate compound and a liquid polyamine. Additionally, it is an object of the invention to provide air care, therapeutic, nutritional, surface treating and pesticidal products made thereby that overcome the disadvantages of the heretofore-known compositions of this general type.

With the foregoing objects in view, there is provided in accordance with the invention a method for preparing air care, therapeutic, nutraceutical, and biocidal compositions and other useful articles. The method includes uniformly immobilizing active liquids such as fragrance oils, pesticides, surfactants, drugs, nutraceuticals, surface active agents, tracer dyes, or other active volatile or non-volatile liquids in a cross-linked matrix selected from the reaction product of a polyamine and a liquid polyepoxy or liquid polyisocyanate material, the reaction being carried out in the presence of the active liquid. Products of this type may be prepared by: (1) blending the polyamine, the active liquid and any desired optional components including diluents, plasticizers, fillers, stabilizers, and colorants; (2) blending this mixture with the polyepoxy or polyisocyanate component optionally diluted with further amounts of plasticizers, fillers, stabilizers, and colorants; (3) pouring out the final blend as a sheet or slab or into a support, form, container, or mold; (4) optionally covering or sealing the poured blend to protect it from contaminants and prevent volatile components from evaporating; (5) optionally storing it until the blend cures; and (6) optionally removing the cured immobilized liquid article from the sheet, slab, form, container, or mold and cutting it to another shape or using it as made in the container.

One invention of the instant application is a visually attractive solid air freshener, in particular a room, closet, drawer, bag, area, container, or car interior freshener, that is both transparent or nearly transparent (e.g. "frosted") and robust. In accordance with this object of the invention, the active liquid is an aromatic composition (i.e. fragrance oil, scent, or perfume). "Robust" means that the article can be packaged inexpensively and handled without being deformed. The composition containing the aromatic material may be supported (i.e., in a container or holder) or free-standing. In particular, no special care is needed when the air freshener is taken out of its package or wrapper. Furthermore, the air freshener according to the invention is intended to resist changes in temperature, humidity, and exposure to light over the lifetime of its use or, with reasonable protection in a suitable package, over the lifetime of its storage and handling. The air care composition is intended to be free of syneresis (also known as "sweating"). The matrix material of the product is to be effectively non-toxic and not cause skin irritation if handled out of its storage wrapper. The air care composition of the present invention lends itself readily to, but does not require the use of, porous powders, fabrics or fibers as a support for the fragrance oil.

A further aspect of the invention is that the article components may be insoluble in water without losing any of the desired final properties (e.g. fragrance release, stability) so that the water may optionally serve some useful purpose if incorporated in the cross-linked composition such as causing shrinkage to indicate end-of-use-life or introduction of a water-soluble active ingredient such as a dye or a salt.

In accordance with a further object of the invention, the active liquid may be and/or contain a bioactive material such as a deodorizer, malodorant, sanitizer, insecticide, pesticide, repellant, or pheromone. For the latter four cases, the product would thus be a pest control device.

In accordance with a further object of the invention, the active liquid may be and/or contain a surface-treatment agent such as a size, a cross-linking or catalytic substance, a surfactant, a stain or other colorant or specialized dye, a fabric softener, or a lubricant.

In accordance with a further object of the invention, the active liquid may be and/or contain a therapeutic, nutritional, and/or bioceutical agent. Thus, the invention may relate to a means for delivering a biomedical product to a human and/or animal patient, such as a patch, or for luring an animal to a trap or hook, as bait.

In accordance with a further object of the invention, the active liquid may be and/or contain a biopolymer such as DNA, RNA, and/or protein, and/or a carbohydrate and/or a steroid. All protected precursors of the same are envisioned by the present invention. Thus, the invention relates, in part, to a bio analytical article and/or a biosensor for diagnostic purposes of patients, experimental subjects, and/or environmental factors.

In accordance with a further object of the invention, an inert solid material may be incorporated to make it more attractive and/or useful. Examples of such materials include, but are not limited to flakes, filings, glitter, foil, beads or chips of mica, metal, plastic, shell or glass polycarbonate flakes, glass beads, or a natural material such as coffee grounds. A possible use for an article containing the latter material is as a novelty coffee-mug coaster. The material could be a clear plastic film pre-printed with a design or logo. Another useful solid object that could be incorporated is a magnet to allow the cross-linked article to cling to metal surfaces. Another useful solid object that could be incorporated is a pest bait material such as sugar, ground nuts, protein powder, and salt.

The instant invention also encompasses a method. The method includes the steps of blending, preferably at or near room temperature, an active liquid such as a fragrance or pesticide, a liquid polyepoxy, polyanhydride, or polyisocyanate compound (hereafter referred to simply as "epoxy", "anhydride" or "isocyanate"), and a liquid or low-melting polyamine; pouring the mixture into a mold or porous support or casting it into a thin sheet; optionally sealing the uncross-linked (e.g. uncured) or partially cross-linked article in an impervious foil or film or container to prevent loss of any active component and leaving the mixture undisturbed at room temperature or, optionally, at an elevated temperature until it has cross-linked (e.g. cured). The resulting thermo-set solid is useful as a component in a device that releases the active component into the environment at a rate depending a number of factors, which may include the geometry of the product, the amount of exposed surface, the temperature, air flow and water movement around it under use conditions, abrasion of the product in use, and the concentrations in the formulation of the active liquid.

There are numerous advantages to immobilizing active materials in the composition and/or article according to the aspect of the invention where the active liquid is immobilized within the cured polymeric matrix and the cured polymeric matrix is a reaction product of a compound having at least two functional groups selected from epoxy, anhydride, and isocyanate with polyamine in the presence of an active liquid, which may include any one or more of the following:

Heat sensitive oils need not be subjected to heat;
High loadings of liquids in a solid product that can be handled are possible;
Product components can be liquids easily blended with simple equipment;
The cure reaction requires no external agent to trigger it, generates no volatile byproducts that might create bubbles, and occurs throughout the mass uniformly;
Little shrinkage of the blend occurs during curing;
Products are transparent if unfilled;
Product components having little odor, color, and toxicity are available;
Products have excellent durability, are insoluble in water, and do not melt.
Products do not adhere to any plastic packaging materials and so can be wrapped in materials that are not special release films;
Cured product tackiness can be adjusted so that products may be tack-free or tacky enough to allow temporary adhesion to a vertical surfaces, e.g. a window;
The product can be readily colored with dyes and pigments; and/or
The fluid pre-cured liquid fills the mold so completely that even fine details are captured as part of the finished product, for example, embossed logos or decorative designs.

Other features that are considered as characteristic for the invention are described herein, and may also be set forth in the appended claims.

Although the invention is exemplified and described herein as embodied in a method for preparing compositions and articles such as transparent, flexible, and stable compositions by immobilizing active liquids with cross-linked matrices, it is nevertheless not intended to be limited to the details shown, since various modifications and structural changes may be made therein without departing from the spirit of the invention and within the scope and range of equivalents of the claims.

Polymeric matrix-immobilized active liquids are useful as air care, pest control, laundry care, therapeutic, or other devices because they release the active ingredient into the ambient environment. The construction and method of operation of the invention, however, together with additional objects and advantages thereof will be best understood from the following description of specific embodiments when read in connection with the accompanying examples and claims.

DESCRIPTION OF THE PREFERRED EMBODIMENTS

The present invention relates to a composition and/or article containing a cross-linked polymeric matrix and an active liquid where the active liquid is uniformly (i.e., homogenously) by (or within) the matrix. The present invention also relates to methods of immobilizing an active liquid within a polymeric matrix. Still further, the present invention relates to methods of making a solid, stable composition and/or article containing a polymeric matrix and an active liquid where the active liquid is immobilized by the matrix. The active liquid may be a solution of active ingredients in a carrier liquid or may be inherently active. The carrier liquid may be an organic liquid or water.

The cross-linked polymeric matrix is a reaction product of a compound having at least one and preferably two or more functional groups selected from the group consisting of epoxy, isocyanate, anhydride, and acrylate and a polyamine compound, the reaction being carried out in the presence of the active liquid. Water, if present and compatible with the matrix, will be part of the immobilized liquid. Water, if present but incompatible with the matrix, may be trapped by the matrix plus immobilized liquid phase or may suspend the matrix/immobilized liquid phase in the form of a particle dispersion.

While the compound having preferably two or more epoxy functional groups can be any epoxy, it is preferably in the form of a liquid. While examples of the epoxy containing compound of the present invention can be found in "Handbook Of Epoxy Resins" by Henry Lee and Kris Neville (McGraw Hill, 1967), "The Epoxy Formulators Manual" by the Society of Plastics Industry, Inc. (1984), and the Encyclopedia of Science and Technology (Kirk-Othmer, John Wiley & Sons, 1994), specific examples of liquid epoxy resins that may be of use in this invention are, but are not limited to, listed below. The examples use the following ingredients: EPON® 828 (the diglycidyl ethers of bisphenol A and F (available as EPON® 828 and EPON® 8620 from Resolution Performance Products), hydrogenated glycidyl ether of bisphenol A (available as EPALLOY® 5000, and EPALLOY® 5001, (products of CVE Specialty Chemicals that include the hydrogenated glycidyl ethers of bisphenol A), the diglycidyl ethers of butanediol, cyclohexane dimethanol, neopentyl glycol, dimer acid, and trimethylolpropane (all available from Resolution Performance Products in their HELOXY® Modifier product line).

The above-mentioned epoxy-containing compounds are merely representative and many additional epoxy-containing compounds are applicable in the present invention.

While the compound having preferably two or more anhydride functional groups can be any polyanhydride, it is preferably in the form of a liquid and is not a male ated polyolefin rubber. More specifically, the preferably anhydride is a solid polymer dissolved in a suitable carrier liquid, the polymer being selected from the group consisting of:

(a) maleated olefin polymers other than a maleated rubber, e.g. a polybutadiene or a poly(isobutylene);

(b) olefin-maleic anhydride co-polymers; and (c) alpha-olefin-maleic anhydride alternating co-polymers, Specific examples of suitable anhydride-functional polymers of the invention are styrene-maleic anhydride copolymers such as DYLARK® 232 and DYLARK® 332 available from NOVA Chemicals and poly(1-octadecene-alt-maleic anhydride), available from Chevron Corporation. These anhydride-containing polymers are representative and many additional anhydride-containing polymers are applicable in the present invention.

While the compound having preferably two or more isocyanate functional groups can be any polyisocyanate, it is preferably a compound in the form of a liquid. Specific examples of the isocyanate-containing compound of the present invention can be any aliphatic difunctional isocyanate material including liquid diisocyanates such as isophorone diisocyanate and bis(4-isocyanato cyclohexyl) methane. Preferred polyfunctional isocyanates are of low volatility and thus reduced toxicity. Examples are those available from Bayer Corporation, Industrial Chemicals Division, under the trade names "DESMODUR®" including without limitation, the DESMODUR® N-series aliphatic isocyanurates, especially DESMODUR® N-3300, DESMODUR® N-3600 and DESMODUR® N-3800, and the DESMODUR® Z-series, especially DESMODUR® Z4470. These isocyanate-containing compounds are representative and additional isocyanate-containing compounds are applicable in the present invention.

As is discussed further below, the isocyanate functional group reacts with an amine functional group significantly faster than does the epoxy functional group so that polyamine compounds suitable for the cross-linking reaction with isocyanates are not necessarily satisfactory for use with epoxies. A preferred polyamine compound of this invention for reaction with epoxy-functional compounds is a liquid at 25° C., dissolves in, and is compatible with, many active liquids, has a viscosity, measured at 100° C., of no greater than about 100 cP, and has an amine number of from 100 to 1200 meq KOH/g. The amine number may be 100, 200, 500, 750, 1000 and 1200 meq KOH/g, including any and all ranges and subranges there between. Preferred polyamines are, but are not limited to: 1,2-diaminocyclohexane, isophorone diamine, meta-xylene diamine, 1,3-bis(aminomethyl)cyclohexane (1,3-BAC). Especially preferred are poly(alkyleneoxy) polyamines (also referred to as polyether amines) liquid at 25° C. and comprising polyether segments such that greater than 50% by weight of the amine is polyether derived from oligomerized ethylene oxide, propylene oxide, butylenes oxide or tetrahydrofuran or combinations of these supplied by, for example, Huntsman Corporation and BASF Corporation. Examples of such are JEFFAMINE® D-230, D-400, D-2000, T-5000, T-403, and XT J511 XTJ-511, all polyether diamines (provided by Huntsman Corporation). Liquid polyamines may also be chosen from the polyamido-amine family, examples of which are the UNIREZ® series of amidoamide-amine curing agents offered for sale by Arizona Chemical. These materials are known to impart adhesion and have lowered skin sensitivity. Amines may be mixtures of two or more amines blended to optimize viscosity, reaction rate and product performance.

The preferred polyamine compound of this invention for reaction with isocyanate-functional compounds is a material having a polymeric backbone comprising repeating monomer units terminated by amine groups that are not part of the monomer unit. This polymeric polyamine, further, is preferably a liquid at a temperature below 50° C., e.g. a liquid or low melt point amine. More preferably, the polyamine is a liquid at normal room temperature. According to the invention, the amine has a melting or softening point below 50° C., including at most 50° C., 45° C., 40° C., 30° C., 20° C., and 10° C., including any and all ranges and subranges there between. Most preferably, the polyamine is a liquid and/or tacky and/or a semisolid at a temperature below 10° C.

Further, the preferred polymeric polyamine dissolves in, and is compatible with, many active liquids, has a number-average molecular weight of greater than 1,000, and has an amine number of from 10 to 100 meq KOH/g, and has a viscosity, measured at 150° C., of no greater than about 500 cP. The amine number may be 10, 25, 50, 75, or 100 meq KOH/g, including any and all ranges and subranges there between. Further, the viscosity, measured at 150° C., of the polyamine may not be greater than about 500 cP. The viscosity, measured at 150° C., of the polyamine may be about 450, 350, 250, 150, and 100 cP, including any and all ranges and subranges there between.

The most preferred polymeric polyamine for reacting with isocyanate-functional compounds of this invention is a polyamide polyether block copolymer resulting from reaction of one or more polyalkyleneoxy polyamines with one or more aliphatic polyacids as further described below and in the example section of this application. Such ether-based polyamide polyamines (or "PAPA") useful in the present invention can be made by reacting a polyacid or mixture of polyacids with a stoichiometric excess of polyether polyamine admixed with optional lower diamines including piperazine, ethylene diamine, isophorone diamine, hexamethylene diamine, 2-methyl-1,5-pentane diamine, and the like. Preferred polyacids for the preparation of PAPA are adipic acid, azeleic acid, sebacic acid, dodecandioic acid or other aliphatic diacid or its ester equivalent. Use of such diacids and a majority amount of poly(alkyleneoxy)polyamine, determined as >50% of all amine equivalents present, ensures that the resulting polyamide will have good solubility in a wide range of liquids including in certain cases, water. Also important to the proper reactivity of the matrix components is the amine number of the PAPA, which should be less than 100, as measured by titration with dilute alcoholic hydrochloric acid and expressed as mg KOH/g sample and preferably less than 80 mg KOH/g and most preferable less than 70 mg KOH/g.

Another preferred PAPA is the reaction product of polymerized fatty acid, also known as dimer acid (material produced by Arizona Chemical Company under the trade name "UNIDYME®", Unichema Corporation under the name "PRIPOL®", and Cognis Corporation under the trade name "EMPOL®") and a stoichiometric excess of one or more poly(alkyleneoxy)polyamines chosen from the group of Huntsman JEFFAMINE® polyamines, including, for example, D-400, D-2000, T-403, and XTJ-500, such that, after the reaction is complete, the polymeric polyamine product is a liquid at room temperature, has an acid value of less than about 5 and an amine value of from about 10 to about 70, and has a viscosity of less than 500 cP measured at 150° C. Most preferred is a PAPA that is a liquid at room temperature, has an acid value of less than 2 and an amine value of 20-60, and has a viscosity of less than 300 cP at 150° C. Thus, for example, a particularly preferred polymeric polyamine is that obtained by reacting PRIPOL® 1009 hydrogenated dimer acid, 29.5 weight %, JEFFAMINE® D-2000, 44.5 weight %, JEFFAMINE® D-400, 22.5 weight %, and JEFFAMINE® T-403, 3.5% at 215° C. under a sweep of dry nitrogen until the acid number drops to about 1.0 and the amine value is adjusted to be about 30-40 (see Example #21, below). This material is a viscous liquid at room temperature with a viscosity of about 100 cP at 130° C. and a weight average molecular weight of about 25,000.

Reaction rate of formation of the matrix of the invention varies with the type of amine present at the termini of the polymeric polyamine component. Lowest cure times result from the use of a compound whose polymer chain terminates in an aliphatic primary or secondary amine. Amines hindered by substitution with a bulky group such as a tertiary butyl moiety react more slowly. Longest cure times result from the use of a polymeric polyamine terminated with a certain type of aromatic amine whose aromatic ring bears a carbonyl, particularly an ester or amide group, or other strong electron-withdrawing group. While it is believed that the carbonyl-substituted aromatic amines may be utilized for reaction with any of the functional groups of this invention, they are particularly useful when the functional group is the highly-reactive isocyanate group.

While any such terminal carbonyl-substituted aromatic amine is believed to be suitable, non-limiting examples of preferred polyamines are those derived from para-amino benzoic acid and ortho-amino benzoic acid. These compounds are readily incorporated onto the termini of polyamides described herein by reaction with the specified polyamines along with the specified diacids. A preferred PAPA of the instant invention is, then, a polymer produced by reacting any of the above-described diacids and ether diamines in the presence of para-amino benzoic acid and/or ortho-amino benzoic acid. For example, a particularly preferred PAPA is that obtained by reacting PRIPOL® 1009 hydrogenated dimer acid, 24.0 weight %, para-aminobenzoic acid, 5.0 weight %, JEFFAMINE® D-2000, 54.0 weight %, JEFFAMINE® D-400, 11.5 weight %, and JEFFAMINE® T-403, 5.5 weight % at 215° C. under a sweep of dry nitrogen until the acid number drops to about 1.0 and the amine value is adjusted to 15 by non-potentiometric titration and 30-35 by potentiometric titration (see Example #36, below). This material is a viscous liquid at room temperature with a viscosity of about 250 cP at 130° C. and a weight average molecular weight of about 13,000 daltons.

In all such PAPA embodiments, the weight-average molecular weight (Mw) and/or number-average molecular weight (Mn) of the PAPA may be as high as desired but is limited by the desired amine value and viscosity. For example, the Mw is preferably in the range 5,000-35,000, more preferable in the range 10,000-30,000 daltons. Accordingly, the polydispersity may be any value but is desirably greater than 1.5 and less than 6, preferably in the range 2.0-4.0 including any and all ranges and subranges there between.

Co-diacids and co-diamines may be employed in minor amounts in preparing PAPA of the invention, that is, less than 50% on an equivalents basis, as long as the desired properties of the PAPA are obtained. Co-diacids may be, for example, adipic acid and similar linear aliphatic diacids. Co-diamines may be, for example, ethylene diamine, piperazine, 1,2-diaminocyclohexane, isophorone diamine, 1,3-bis(aminomethyl)cyclohexane, dimer diamine (e.g. VERSAMINE® 551), hexamethylene diamine, 2-methyl-1,5-pentane diamine, and similar linear, branched and cyclic aliphatic diamines. The polyamidification reaction may be carried out in the presence of catalysts known to increase the reaction rate such as acids, particularly para-toluene sulfonic, phosphoric and sulfuric acids, and with removal of water of reaction via application of a vacuum.

PAPA that are not liquids at room temperature, that are instead solids at room temperature (e.g. low melting polyamines) and are compatible with the active liquids of this invention, are operable in the instant invention. Such a PAPA results from the reaction of a major diacid portion of 1,4-cyclohexane dicarboxylic acid and a stoichiometric excess of polyamine, the majority of which is a poly(alkyleneoxy) polyamine chosen from the group of Huntsman JEFFAMINE® polyamines, including, for example, D-400, D-2000, T-403, and XTJ-500 such that, after the reaction is complete, the PAPA is a solid at 25° C., has an acid value of less than 5 and an amine value of from about 10 to about 70, and has a Ring & Ball softening point less than 50° C. For these polyamides, dimer acid may optionally be used as a co-diacid along with other co-diacids such as those mentioned above. Co-diamines likewise are optional but not desired components since their presence even at low levels is sufficient to raise the softening point of the PAPA over 50° C.

The polymeric polyamines of the present invention may also be those polyamines described in U.S. Pat. Nos. 6,870,011 and 6,399,713, as well as U.S. patent application Ser. No. 10/395,050, all such patents and patent applications are hereby incorporated, in their entirety, herein by reference.

The active liquid of the present invention may be any liquid that imparts upon the resultant composition and/or article a function. That is, the active liquid may be a volatile or non-volatile organic liquid or a semi-solid or a solid dissolved in a carrier liquid (diluent). Examples of such active liquids include fragrance oils, surface treating chemical, nutraceuticals, drugs, radio-tracers, pesticides, and surfactants.

One non-limiting example of an active liquid is fragrance oil (also called scent or perfume). A fragrance oil can be any blend of the large number of synthetic aroma chemicals and aromatic natural oils known to the perfumer's art. Some of the classes of chemicals useful in the instant invention are esters such as linalool acetate and butyl acetate (present in banana oil), phenols such as methyl salicylate (present in oil of wintergreen), ethers such as 1,8-cineole (present in eucalyptus oil), alcohols such as geraniol (present in rose oil), aldehydes such as cinnamaldehyde (present in cinnamon oil), and ketones such as menthone (present in spearmint oil).

Specific examples of the many hundreds of commercially available fragrance oils useful in this invention are "Ocean" (N-123-03), "Country Wildflower" (N-122-03), "Spring Meadow" (N-124-03) and "Morning Rain" (Q-119-03) supplier by Continental Aromatics of Hawthorne, N.J.; "Evergreen" (#42441) and "Green Apple" (#50520) supplied by Belle Aire Fragrances of Mundelein, Ill.; "Cherry" (#124559), "Vanilla" (#122745) and "Mulberry" (#124561) supplied by Aromatic Fragrances and Flavors International of Marietta, Ga.; "Garnet" (#242926) supplied by International Fragrances Technology, Inc. of Canton, Ga.; and "Crisp Breeze", "Tropical Fragrance", "Oceanside Mist" supplied by Atlas Products of Tinley Park, Ill. A Table of examples is provided herewith below.

There are hundreds of commercial fragrance oils from scores of suppliers. The present invention is not limited to any particular fragrance, but a list provided in the TABLE, below, exemplifies the vast selection of oils that can be used to make immobilized oils of this invention and thus the dynamic operability of the polymeric matrix of present invention.

| Supplier | Supplier Location | Fragrance Name | Oil Code Number |
| --- | --- | --- | --- |
| Continental Aromatics | Hawthorne, NJ | Ocean | N-123-03 |
| | | Country Wildflower | N-122-03 |
| | | Spring Meadow | N-124-03 |
| | | Morning Rain | Q-119-03 |
| Orlandi, Inc. | Farmingdale, NY | MacIntosh | 9466-16582 |
| Belle Aire | Mundelein, IL | Green Apple | 50520 |
| | | Yankee Home | 50522 |
| | | Evergreen | 42441 |
| Aromatic Flavors and Fragrances | Marietta, GA | Cherry | 124559 |
| | | Vanilla | 122745 |
| | | Downey | 127426 |
| | | Mulberry | 124561 |
| International Fragrances Technology | Canton, GA | Garnet | 242926 |
| Atlas Products | Tinley Park, IL | Crisp Breeze | 4062184 |
| | | Tropical Fragrance | 4062182 |
| | | Oceanside Mist | 4062178 |
| Wessel Fragrances | Englewood Cliffs, NJ | Orange Twist | 11721 |
| | | Linen Fresh | 15051 |
| | | Country Garden | 6959 |

The active liquid is be used at a level so as to impart efficacy to the composition for the intended application. The active ingredient may conceivably be extremely potent and need be present only in a very low level, perhaps less than 0.1%, but must according to the present invention be immobilized as an active liquid by dilution with a carrier liquid. In such a case, the active liquid is said to be the solution of potent agent in carrier. Keeping this sense in mind, then, the active liquid (or potent agent dissolved in carrier) may be used in the compositions and/or articles of the present invention at levels from about 1% for lightly-loaded objects to about 90% or more. The loading will certainly be a function of the particular active liquid, polymer matrix and any other compounds present. It may also depend upon the final configuration of the formed product, that is, whether it is free-standing, contained, or supported. The amount of active liquid may be 1, 2, 5, 10, 15, 20, 30, 40, 50, 60, 70, 80, or 90% inclusive of all ranges and subranges there between.

As a non-limiting example, a preferred fragrance oil level for air fresheners is about 15-75% and the most preferred use level is 30-70% by weight of the finished article not counting the weight of any embedded objects. The amount of fragrance oil may be 15, 20, 25, 30, 40, 50, 60 and 75% by weight of the composition (not counting the weight of any supports or embedded objects) inclusive of all ranges and subranges there between. Inactive diluent or plasticizer can be present in an additional amount such that the total liquid level can be from about 20% to about 90% by weight of the composition, preferably from about 40% to about 80% by weight of the composition.

Similarly, the mixture of reactive components, active liquid and optional liquids, while still uncured, may be dispersed in water or other aqueous medium and the resulting oil-in-water emulsion stabilized by means of a surfactant. Droplets of inventive composition thus emulsified cure. The result is a dispersion of solid immobilized active liquid particles in water. The surfactant may be anionic, cationic, or non-ionic in nature. Examples are the anionic salt sodium lauryl sulfate, the cationic quaternary ammonium salts di(hydrogenated tallow)dimethyl ammonium chloride, cocamido propyl betaine, and dibenzyl dimethyl ammonium chloride, and the non-ionic polyethoxylated sorbitan mono-oleate. Such an emulsion is a milky liquid and can, as such, be impregnated into a porous medium such as paper, cardboard, cellulose pad, cellulose pulp, felt, fabric, a porous synthetic foam, a porous ceramic, activated carbon, soil, diatomaceous earth, kieselguhr, charcoal, silica, clay, and the like or coated onto a non-porous substrate included but not limited to plastic films, metallic foils, rubber, ceramics, wood, glass, and leather.

Surfactant compounds may themselves be active compounds of the invention when used in excess of the amount needed to stabilize the gel dispersion. They may be used with or without water. Surfactants thus immobilized are released slowly into their use environment along with fragrance or other active components, and may thus serve as, for example, a toilet air freshener/cleaner, a pesticide/disinfectant, or a fabric softener in a laundry dryer either in the form of a liquid or, if impregnated into a porous medium, a sheet.

The active liquid of the present invention may be a liquid pesticide or a solid pesticide dissolved in a carrier liquid. A pesticide is any substance or mixture of substances intended for preventing, destroying, repelling, or mitigating any organism that causes or might cause harm or annoyance to humans, valuable animals (e.g. livestock), or valuable plants (e.g. flowers, trees, and food crops).

A pesticide may be a chemical substance or biological agent (such as a virus or bacteria) used to control insects, plant pathogens, weeds, mollusks, birds, mammals, fish, nematodes (roundworms) and microbes that compete with humans for food, destroy property, spread disease or are a nuisance. Because many pesticides are poisonous to humans, it is useful to control their application and release by, for example, dissolving them in a harmless carrier liquid and then immobilizing them with the matrix of the present invention.

Pesticides can be natural or synthetic. Among the synthetic pesticides are:

1. Organo-phosphates. These pesticides affect the nervous system by disrupting the enzyme that regulates acetylcholine, a neurotransmitter. They usually are not persistent in the environment. Immobilization, then, can help them be effective longer without harming the environment.

2. Carbamates that also affect the nervous system by disrupting the enzyme that regulates acetylcholine.

3. Organochlorines that were commonly used in the past, but many have been removed from the market due to their health and environmental effects and their persistence (e.g. DDT and chlordane); and 4. Pyrethroids, developed as synthetic versions of the naturally occurring pyrethrin. The synthetics are modified to increase their stability in the environment and lower their cost.

Some pesticides are derived from such natural materials as animals, plants, bacteria, an example being the naturally-occurring material, pyrethrin, extracted from chrysanthemums. Biopesticides include microbial pesticides that consist of a microorganism (e.g., a bacterium, fungus, virus or protozoan) as the active ingredient. Microbial pesticides can control many different kinds of pests, although each separate active ingredient is relatively specific for its target pest/s. For example, there are fungi that control certain weeds, and other fungi that kill specific insects. The most widely used microbial pesticides are subspecies and strains of *Bacillus thuringiensis*, or Bt.

Pesticides can be classed according to the type of pest that they combat. Useful in the present invention are the following types of pesticides: algicides that control algae in lakes, canals, swimming pools, water tanks, and other sites; antifouling agents that kill or repel organisms that attach to underwater surfaces, such as boat bottoms; antimicrobials that kill microorganisms (such as bacteria and viruses); attractants that attract pests (for example, to lure an insect or rodent to a trap) including foods such as sugar; biopesticides that are active agents derived from natural materials such as animals, plants, bacteria, and certain minerals; biocides that kill microorganisms, disinfectants and sanitizers that kill or inactivate disease-producing microorganisms on inanimate objects, fungicides that kill fungi (including blights, mildews, molds, and rusts); herbicides that kill weeds and other plants that grow where they are not wanted; insecticides that kill insects and other arthropods, miticides (also called acaricides) that kill mites that feed on plants and animals, microbial pesticides that are microorganisms that kill, inhibit, or out compete pests, including insects or other microorganisms; molluscicides that kill snails and slugs, nematicides that kill nematodes (microscopic, worm-like organisms that feed on plant roots); ovicides that kill eggs of insects and mites; pheromones that disrupt the mating behavior of insects; repel lents that are chemicals that repel pests, including insects (such as mosquitoes) and birds from a surface such as skin or seeds; rodenticides that sicken, repel, or kill mice and other rodents; insect growth regulators that disrupt the molting, maturity from pupal stage to adult, or other life processes of insects, and plant growth regulators that are substances (excluding fertilizers or other plant nutrients) that alter the expected growth, flowering, or reproduction rate of plants.

Without meaning to be exhaustive, pesticides that can be used in the articles of the present invention are: 2,4-D, 2,4-DB, DCPA (Chlorthal), MCPA, Abamectin, Acephate (Orthene), Acetochlor, Acifluorfen, Alachlor, Aldicarb, Allethrin, Ametryn, Amitraz, Atrazine, Azadirachtin, Azinophos-Methyl, *Bacillus Thuringiensis*, Bendiocarb, Benomyl, Bensulide, Bentazon, Bifenthrin, Bromacil, Bromoxynil, Butylate, Cacodylic Acid, Captafol, Captan, Carbaryl, Carbofuran, Carbophenothion, Carboxin, Chloramben, Chlordane, Chlorobenzilate, Chloropicrin, Chlorothalonil, Chlorpyrifos, Chlropropham, Clethodim, Clomazone, Coumaphos, Cyanazine, Cyfluthrin, Cypermethrin, Dalapon, Daminozide, DEET, DDT, Deltamethrin, Demeton-S-Methyl, Diazinon, Dicamba, Dichlorvos, Diclofop-Methyl, Dicofol, Dicrotophos, Dienchlor, Diflubenzuron, Dimethoate, Dimetomorph, Dinocap, Dinoseb, Diphacinone, DiquatDibromide, Disulfoton, Diuron, Dodine, EthyleneDibromide, Endosulfan, Endothall, EPTC, Esfenvalerate, Ethephon, Ethion, Fenamiphos, Fenitrothion, Fenoxycarb, Fenthion, Fluazifop-p-butyl, Flucythrinate, Fluometuron, Fluvalinate, Folpet, Fonofos, Formothion, Haloxyfop, Heptachlor, Hexachlorobenzene, Hexazinone, Hydramethylnon, Imazalil, Imazaquin, Imazethapyr, Imidacloprid, Iprodione, Isofenphos, Lactofen, lambda-Cyhalothrin, Lindane, Linuron, Malathion, Mancozeb, Maneb, Mecoprop, Metalaxyl, Metaldehyde, Methamidophos, Methidathion, Methomyl, Methoprene, Methoxychlor, Methyl Bromide, Methyl Parathion, Metiram, Metolachlor, Metribuzin, Metsulfuron-Methyl, Mevinphos, Molinate, Monocrotophos, Naled, Napropamide, Nicosulfuron, Oryzalin, Oxamyl, Oxyfluorfen, Paraquat, Parathion, Pendimethalin, Pentachlorophenol, Permethrin, Phorate, Phosalone, Phosmet, Picloram, Primisulfuron-Methyl, Prometryn, Pronamide, Propanil, Propazine, Propetamphos, Propoxur, Pyrethrins and Pyrethroids, Quintozene, Quizalofop-p-Ethyl, Resmethrin, Rotenone, Ryania, Scilliroside, Sethoxydim, Simazine, Streptomycin, Sulfometuron-Methyl, Tebuthiuron, Temephos, Terbacil, Terbufos, Terbutryn, Thiabendazole, Thiram, Triadimefon, Triallate, Trichlorfon, Triclopyr, Trifluralin, Triforine, Validamycin, Vemolate, Vinclozolin, Warfarin, Zineb, and Ziram.

The present invention is also useful for immobilizing liquid pheromones or solid pheromones dissolved in a carrier liquid and, therefore, for producing articles that may serve as baits or lures in insect traps, fishing lures, rodent traps, and the like. Pheromones are typically six-to-twenty carbon atom esters, aldehydes, alcohols and ketones and for that reason resemble fragrance compounds and can be immobilized as described earlier for fragrance compounds. There are many hundreds of such compounds identified for many animal and insect species, many of which are not considered pests. Representative examples that can be used in the articles of the present invention include, without being exhaustive: E or Z-13-octadecenyl acetate, E or Z-11-hexadecenal; E or Z-9-hexadecenal; hexadecanal; E or Z-11 hexadecenyl acetate; E or Z-9-hexadecenyl acetate; E or Z-11-tetradecenal; E or Z-9-tetradecenal; tetradecanal; E or Z-11-tetradecenyl acetate; E or Z-9-tetradecenyl acetate; E or Z-7-tetradecenyl acetate; E or Z-5-tetradecenyl acetate; E or Z-4-tridecenyl acetate; E or Z-9-dodecenyl acetate; E or Z-8 dodecenyl acetate; E or Z-5-dodecenyl acetate; dodecenyl acetate; 11-dodecenyl acetate; dodecyl acetate; E or Z-7-decenyl acetate; E or Z-5-decenyl acetate; E or Z-3-decenyl acetate; octadecanal, Z or E, Z or E 3,13-octadecadienyl acetate; Z or E, Z or E 2,13-octadecdienyl acetate; Z, Z or E-7,11-hexadecadienyl acetate; Z, E 9,12-tetradecadienyl acetate; E, E-8,10-dodecadienyl acetate; Z, E 6,8-heneicosadien-11-one; E, E 7,9-heneicosadien-11-one; Z-6-henicosen-11-one; 7,8-epoxy-2-methyloctadecane; 2-methyl-7-octadecene, 7,8-epoxyoctadecane, Z,Z,Z-1,3,6,9-nonadecatetraene; 5,11-dimethylheptadecane; 2,5-dimethylheptadecane; 6-ethyl-2,3-dihydro-2-methyl-4H-pyran-4-one; methyl jasmonate; alpha-pinene; beta-pinene; terpinolene; limonene; 3-carene; p-cymene; ethyl crotonate; myrcene; camphene; camphor; 1,8-cineole; alpha-cubebene; allyl anisole; undecanal; nonanal; heptanal; E-2-hexenal; E-3-hexenal; hexanal; verbenene; verbenone; verbenol; 3-methyl-2-cyclohexenone; 3-methyl-3-cyclohexenone; frontalin; exo and endo brevicomin; lineatin; multistriatin; chalcogran; 7-methyl-1,6-dioxaspiro(4,5-decane, 4,8-dimethyl-4(E),8(E)-decadienolide; 11-methyl-3(Z)-undecenolide; Z-3-dodecen-11-olide; Z,Z-3,6-dodecen-11-olide; Z-5-tetradecen-13-olide; Z,Z-5,8-tetradecen-13-olide; Z-14-methyl-8-hexadecenai; 4,8-dimethyldecanal; gamma-caprolactone; hexyl acetate; E-2-hexenyl acetate; butyl-2-methylbutanoate; propylhexanoate; hexylpropanoate; butylhexanoate; hexylbutanoate; butyl butyrate;

E-crotylbutyrate; Z-9-tricosene; methyl eugenol; alpha-ionone; 4-(p-hydroxyphenyl)-2-butanone acetate; E-beta-famasene; nepetalactone; 3-methyl-6-isopropenyl-9-decenyl acetate; Z-3-methyl-6-isopropenyl-3,9-decadienyl acetate; E or Z-3,7-dimethyl-2,7-octadecadienyl propionate; 2,6-dimethyl-1,5-heptadien-3-ol acetate; Z-2,2-dimethyl-3-isopropenyl cyclobutanemethanol acetate; E-6-isopropyl-3,9-dimethyl-5,8-decadienyl acetate; Z-5-(1-decenyl)dihydro-2 (3H)-furanone; 2-phenethylpropionate; 3-methylene-7-methyl-7-octenyl propionate; 3,11-dimethyl-2-nonacosanone; 8-methylene-5-(1-methylethyl)spiro(11-oxabicyclo) 8.1.0-undecene-2,2-oxiran-3-one; 2-propylthietane; 3-propyl-1,2-dithiolane; 3,3-dimethyl-1,2-dithiolane; 2,2-dimethylthietane; E or Z-2,4,5-trimethylthiazoline; 2-sec-butyl-2-thiazoline; and isopentenyl methyl sulfide. Specific pheromones include the following: 8-methyl-2-decyl-propionate; 14-methyl-1-octadecene; 9-tricosene; tridecenyl acetate; dodecyl acetate; dodecenyl acetate; tetradecenyl acetate; tetradecadienyl acetate; hexadecenyl acetate; hexadecadienyl acetate; hexadecatrienyl acetate; octadecenyl acetate; dodecadienyl acetate; octadecadienyl acetate; Z,E-9,12-tetradecadiene-1-ol.

The active liquid may be a liquid form of the active ingredient, or may be a solid, liquid or gaseous form of the active ingredient that is dissolved (contained) and diluted by a carrier liquid (diluent). The active liquid may consist of water and an active agent dissolved in the water. The active liquid may consist of an organic liquid and an active agent dissolved in the liquid.

Examples of active ingredients contained in the active liquid may be therapeutically active ingredients (for humans or animals) such as medicines, drugs, pharmaceuticals, bioceuticals which are optionally combined with a biologically-acceptable carrier. Further, examples of the active ingredient contained in the active liquid may be biological compound such as an amino acid, vitamin, carbohydrate and/or steroid. Examples of the biological compound may be a biopolymer or biocopolymer or chimera comprising DNA, RNA, oligonucleotides, modified DNA, modified RNA, proteins, polypeptides, and modified polypeptides.

In addition to preferred embodiments described above, additional embodiments are possible by adding/changing the optional components, including the plasticizer, diluent, accelerators, retardants, tackifiers, fillers, and colorants. Phthalates, benzoates, salicylates, and lactate esters, alcohols, polyols, poly(alkylene glycol)s and alkyl and aryl ethers of alcohols, polyols and poly(alkylene glycols) are examples of useful plasticizers/diluents. These increase product flexibility, improve active release, and lower product cost.

Factors that can be used to affect epoxy-based products can be applied to the invention of the instant application as well. These materials may well impart benefits to the air fresheners of this invention. Reactive diluents and inert diluents may also be used to lower the initial blend viscosity. Possible diluents include, but are not limited to, various mono- and diglycidyl ethers, glycols, and N-methylpyrrolidinone. Phenols such as nonyl phenol and 2,4,6-tris(dimethylaminomethyl) phenol are examples of possible known accelerators of the epoxy-amine curing reaction. Therefore, they may benefit the system by shortening the time needed to cure the air fresheners of this present invention. Reaction accelerators may be any alcohol-containing compound and/or water and/or mixtures thereof. Dissolving certain resins in the epoxy or the diluent/plasticizer and adding them to the system may impart tack to the final product. These include rosin esters and polyterpenes sold by Arizona Chemical under the trade names SYLVATAC®, SYLVARES®, and SYLVALITE®.

The composition and/or article of the present invention may be made by contacting, mixing, or blending a compound containing preferably two or more functional groups selected from epoxy, isocyanate, anhydride, and acrylate with a polyamine compound in the presence of an active liquid. The resultant mixture prior to and after curing is preferably homogeneous. Such contacting, mixing, and blending of the reactive components and active liquid may occur at a temperature from 10-50° C. The blending operation temperature may preferably be 10, 15, 20, 25, 30, 35, 40, 45 and 50° C., inclusive of all ranges and subranges there between. The components may be added in any order consecutively with the proviso that active liquid cannot be added after the matrix-forming reaction proceeds to a point where its high viscosity and increasing elasticity precludes a blending operation. Optional ingredients may be added to the mixture in any order, again with the proviso mentioned above. In instances when the amine is a solid, it is preferably first dissolved in diluent liquid or in the active liquid or in a mixture of both.

Temperature and blending conditions must be controlled so as to preclude premature curing, that is extensive curing during the contacting, mixing, or blending step. Preferably the mixture will become a homogeneous thermo-set solid thereafter. Curing temperatures may be different from blending operation temperatures and may be in the range from 10-100° C., preferably 10, 20, 30, 40, 50, 60, 70, 80, 90, and 100° C., inclusive of all ranges and subranges there between.

Curing rate is a function of at least six factors: curing temperature, functional group and amine group concentrations, ratio of these, structure of the amine, accelerator/retardant concentration, and composition of the fragrance oil/diluent. Accordingly, cure times can vary widely.

Mixing and/or curing can occur within a mold. For example, a low temperature procedure may include blending at room temperature, pouring the blend into a mold, sealing it, and allowing the blend to stand at room temperature. Such a procedure may take from a few minutes to a few days depending on the functional groups chosen and the reaction conditions. For example, the isocyanate-amine matrix reacts significantly faster than the epoxy-amine matrix. Another example is a pre-curing procedure useful more for the epoxy-amine matrix, which consists of blending at room temperature, sealing tightly, heating to 70° C. for 30-90 minutes to obtain a partial cure but not gelling the composition, then pouring the resultant partial cure into a mold, letting it cool and stand at room temperature. Such a procedure may take from an hour to two days. Finally, another example is a high temperature procedure which may include blending at room temperature, pouring into a pouch or mold, sealing it tightly, and heating it to a temperature ranging from 60 to 100° C. Such a procedure may take from a few minutes to a few hours.

The method of the instant invention is not limited to the above steps in that order and one may very well wish to combine different steps therein. In addition, the curing time may range from 0.01 hour to 60 hours, more preferably from about 5 minutes to 20 hours, and most preferred from 10 minutes to 100 minutes, that is 10, 20, 30, 40, 50, 60, 70, 80, 90, and 100 hours, inclusive of all ranges and subranges there between.

A preferred embodiment of the present invention includes blending an active liquid, a liquid polyepoxy, and a liquid polyamine to form a mixture. Blending the components may occur at 10-40° C. However, the blending is performed so as not to cause a loss of any temperature-sensitive active component. The temperature of blending may preferably be 10, 15, 20, 25, 30, 35, and 40° C., inclusive of all ranges and subranges there between. When an epoxy-containing compound is used, the temperature of curing can be room temperature, i.e. 25° C., but may be higher, depending on the temperature sensitivity of the active liquid component and its volatility. If the active liquid does not degrade readily and the curing is performed in a sealed mold, a preferred curing temperature is about 60° C. At this temperature, curing for a typical formulation takes place in about 3-6 hours, or less if accelerator is used.

An additional preferred embodiment of the present invention consists of blending an active liquid, a liquid diluent, a liquid polyisocyanate, and a liquid polyamine to form a mixture that cures to a liquid-immobilized polyurea composition. Blending the components may occur at 10-40° C. However, the blending is performed so as not to cause a loss of any temperature-sensitive active component. The temperature of blending may preferably be 10, 15, 20, 25, 30, 35, and 40° C., inclusive of all ranges and subranges there between.

The reaction between a polyamine and an isocyanate is rapid at room temperature even in the absence of a catalyst. Preferably a catalyst is not present; rather it is preferred that a rate modifier, or "retardant", be used to slow the reaction, allowing ample time for the ingredients to be blended and poured into a mold. Useful rate modifiers are, for example, aldehydes such as those normally present in common essential oils and fragrance oils. Others are those that are either bland in odor or enhance the odor of the active liquid. Examples of useful retardants are aromatic aldehydes such as benzaldehyde, vanillin, and salicylaldehyde; $\alpha,\beta$ unsaturated aromatic aldehydes such as cinnamic aldehyde and methyl cinnamic aldehyde; terpenic aldehydes such as citral, cyclocitral, and citronellal; and $C_4$-$C_{18}$ aliphatic and cycloaliphatic aldehydes such as isobutyraldehyde, lyral, 2-phenyl propionaldehyde and the like. While a retardant described above may be preferred when an isocyanate-containing compound is used according to the present invention, such a retardant may be optionally utilized in all of the reactions according the present invention.

Another method for increasing cure times is to employ PAPA terminated with a carbonyl-substituted aromatic amine whose preparation is discussed above. The TABLE below lists the set times (time from mixing to lack of flow) for four commercial fragrances immobilized at 50% concentration with matrix derived from the reaction of PAPA and DESMODUR® N3300, the PAPA being terminated either by a non-aromatic primary amine or by a carbonyl-substituted aromatic amine, i.e., the PAPA terminated by reaction with para-aminobenzoic acid.

| | TIME TO SET (minutes) | |
|---|---|---|
| Fragrance Oil | PAPA with Non-Aromatic Primary Amine | PAPA with para-Amino-Benzoic Acid Termination |
| Outdoor Breeze | ca. 0.2 | 400 |
| Tropical Splash | 34 | 420 |
| Clean Citrus | 39 | ca. 20 hours |
| Cotton Fresh | 54 | ca. 30 hours |

When an isocyanate-containing compound is utilized, a preferred temperature of curing is room temperature, i.e. 25° C., but may be higher or lower, depending on the cure time desired. For example, if the active liquid does not degrade readily and a very rapid cure is desired, the curing may be carried out in a sealed mold, and at a preferred curing temperature of about 50° C. At room temperature, curing for a typical formulation based on PAPA terminated by a primary aliphatic amine and carried out in the presence of little or no retardant, typical setting times are from less than 1 second to about 30 minutes. The time may be 0.1, 0.5, 1, 5, 10, 20, and 30 minutes, including any and all ranges and sub ranges there between. Curing at room temperature for a typical formulation based on the carbonyl-substituted aromatic amine terminated polyamine takes place in from about 10 minutes to over 2 days when carried out in the presence of retardant but is preferably in the range 20-600 minutes in the absence of retardant. The time may be 20, 50, 100, 200, 300, and 600 minutes, including any and all ranges and subranges there between.

The instant invention relates, in part, to a composition and/or article comprising a cross-linked polymeric matrix and an active liquid where the active liquid is immobilized within the cross-linked polymeric matrix and the cross-linked polymeric matrix is a reaction product of a compound having at least one and preferably two or more functional groups selected from epoxy, anhydride, and isocyanate with a polyamine compound in the presence of the active liquid. Numerous advantages to immobilizing active liquids in this manner include:

Heat sensitive oils need not be subjected to heat;

High loadings of liquids in a solid product that can be handled are possible;

Product components can be liquids easily blended with simple equipment;

The cure reaction requires no external agent to trigger it, generates no volatile byproducts that might create bubbles, and occurs throughout the mass uniformly;

Little shrinkage of the blend occurs during curing;

Products are transparent if unfilled;

Product components having little odor, color, and toxicity are available;

Products have excellent durability, are insoluble in water, and do not melt.

Products do not adhere to any plastic packaging materials and so can be wrapped in materials that are not special release films;

Cured product tackiness can be adjusted so that products may be tack-free or tacky enough to allow temporary adhesion to a vertical surfaces, e.g. a window;

The product can be readily colored with dyes and pigments;

The fluid pre-cured liquid fills the mold so completely that even fine details are captured as part of the finished product, for example, embossed logos or decorative designs.

When the composition contains a cross-linked polymeric matrix based on the reaction of a compound bearing epoxy functional groups, there are two additional advantages:

Blends cure slowly at room temperature even when an aliphatic primary amine-terminated polyamine compound is used thus allowing ample time for the uncured material to be degassed, optional fillers and/or icons to be added, the uncured material transferred or pumped and poured into molds and the molds stored before the matrix-liquid blend-sets.

A large variety of polyamines are available allowing final cross-linked product properties to be controlled.

When the composition contains a cross-linked polymeric matrix based on the reaction of a compound bearing isocyanate functional groups and a PAPA, there are two additional advantages:

Blends cure rapidly at room temperature, often within 30 minutes.

PAPA, unlike other polyamine compounds, are high molecular weight polymers having little or no odor, high viscosity, low color and low toxicity.

The instant method for immobilizing active liquids can be adjusted to overcome or avoid the following exemplified drawbacks:

Curing is exothermic but the heat generated in blends of this invention, in which the active liquids is a major component, is unnoticeable, especially when blends are allowed to cure in small molds with inherently good heat dissipation.

Epoxy curing is slow, often requiring 1-3 days at 25° C. but is desirably done in the mold after the product is sealed and packaged. Cure times may be significantly reduced by the use of accelerators and by heating the article to about 60° C.

Isocyanate curing in some cases is so rapid that the blend cannot be poured into a mold. This can be avoided by proper choice of the blend temperature, retardant, PAPA, and the concentrations of reactants.

All amine compounds are inherently somewhat toxic and require care in handling but are used in relatively low levels and become irreversibly incorporated into the cross-linked polymer matrix during the curing process. Only traces of free amine groups are present in the cross-linked product.

All isocyanate compounds are inherently also somewhat toxic and require care in handling but are used in relatively low levels in the inventive compositions. Only traces of free isocyanate are present in the cross-linked product and even these are eliminated over time by further reaction with alcohols in the active liquid, diluent, or water. The epoxy resin is EPALLOY® 5001. The hardeners are T-403, IPDA, and 1,3-BAC. The fragrance oil is "Evergreen" supplied by Belle Aire Fragrances of Mundelein, Ill.

Many of these are for the purpose of making the article more visually attractive. While not essential to the invention, these materials may well impart benefits to the articles of this invention such as modifying the release rate of the active ingredient contained therein.

The articles of the present invention include but are not limited to medicinal devices having an active liquid that is medicinally active, pesticide devices having an active liquid that is a pesticide, laundry care devices having an active liquid for laundry care (i.e., softener, fragrance, conditioner, cleaner, anti-stain, surface treating, and the like), or air freshener having an active liquid that is a fragrance.

The article of the present invention may be processed into any desired shape that is appealing to a potential consumer. Such shapes can be a 3-D shape formed in a mold or a flat shape stamp-cut from pre-formed thin sheets. Shapes may include those geometrical in nature, e.g. triangular, squares, circular, spherical, oval, regular geometric figure, irregular geometric figure, etc. Due to the immense number of 3-D shapes that may be formed the above-mentioned examples are not meant to be limiting to the articles of the present invention.

Compositions of the present invention as described above comprise fragrance oil or other active liquid immobilized with a matrix. A distinct advantage of the invention is that the essential components are liquids that remain fluid for some period of time after mixing and before curing into the solid, thermoset form. This allows the preparation of a large variety of forms of air care articles. The present invention, then, also comprises these articles and especially articles suitable for use in air care products, especially air fresheners. Air fresheners may include room air fresheners; closet air fresheners; container air fresheners for containers such as boxes, cans, storage containers, bags, trunks, cases, bins, trash container, and/or barrels; vehicle air fresheners; and area/zone air fresheners for areas or zones such as a walkway in front of a business, a walkway in a mall, etc.

Air care articles of the present invention, for example, can have a immense variety of geometric and artistic shapes such as, but not limited to, disks, rings, cylinders, squares, rectangles, pentagons, hexagons, stars, hearts, hemispheres, spheres, cubes, flowers, animals, letters, numbers, logos, trademarks, and faces. Such shapes are limited only by methods known to make appropriate-shaped molds.

These articles may be colored with soluble dyes or with pigments. These colorants are preferable dissolved or dispersed prior to final mixing of the reactive components. These colorants may be conventional, fluorescent, pearlescent, temperature-sensitive, light-sensitive, pH-sensitive, or moisture sensitive. The latter four colorants allow for the preparation of novelty products that change color as environmental conditions change or that signal the depletion of the active component in the article.

Because the composition prior to curing is fluid, it can be poured easily into such molds and thus take on exacting shapes such as dimples, curves, logos, etchings, and any other embossed or engraved image. This is especially advantageous if the article is designed to fit directly into a holder, to adhere to a surface of complex shape, for example, a body part, a curved surface such as a heated potpourri dish, light bulb, or the inside of a package.

Into the reactive mixture prior to curing can be suspended all manner of insoluble matter so that when cross-linked, the system traps the suspended matter. Suspended matter can be decorative items such as icons, beads, glitter, gems, shards and the like; botanicals such as leaves, seeds, stems, needles, nuts, and the like; insoluble powdered materials such as wax, sugar, coffee grounds, bait particles, insoluble plain, colored or flavored salts, water, glycerin, silicone fluids, and aqueous solutions of dyes, active materials, acids, bases and the like with or without the aid of a surfactant to stabilize the dispersion thus formed; or with air or other gas by a whipping action or other deliberate mixing with the gas to form bubbles in the matrix-forming fluid. Alternatively, gas may be generated inside the matrix-forming composition by chemical means, such as, for example, thermal decomposition of a nitrogen-, oxygen-, or carbon dioxide-generating substance. Examples of such compounds are carboxylic acids, azobis(isobutyronitrile), hydrogen peroxide, and sodium carbonate or bicarbonate. A preferred carboxylic acid for use in this way is polymerized fatty acid.

The article of the invention may consist of nothing more than the fragrance oil or other active liquid and components selected from those listed above as immobilized by the cross-linked matrix or the article may consist of the immobilized liquid and a support, be it a container, bracket, or holder into which the mixture of the reactive components, actives and other liquids and optional components are poured before curing takes place or fitted after curing takes place.

If not poured into a container, the article after curing may be coated, printed, or otherwise decorated, wrapped or supported by a stand, plate, bowl, dish, bracket, holder, or other supporting device. If poured into a container, the container may be made of glass, ceramic, metal, paper, plastic, or any other oil-impermeable material and be in any convenient shape such as a cylinder, tube, bowl, dish, etc. The container may itself be shaped to fit into a holder, chamber, or receptacle designed to fit into a fragrance dispensing device that may be fitted with a heater, fan, blower, or other mechanical aid. If the article is intended to be heated, the heater may be external to the cross-linked matrix-immobilized active liquid or it may be internal, that is, surrounded by or embedded in the cross-linked article. An example of such a device is a reactive composition of the invention poured into a container threaded with resistive heating wires that, after the matrix cures, can be electrified, thus heating the cross-linked composition from within.

Similarly, the composition while still fluid may be impregnated into a porous material such as paper, cardboard, cellulose pad, cellulose pulp, felt, fabric, a porous synthetic foam, a porous ceramic, activated carbon, soil, diatomaceous earth, kieselguhr, sand, charcoal, silica, clay, and the like or coated onto a non-porous substrate included but not limited to plastic films, metallic foils, rubber, ceramics, wood, glass, and leather.

Similarly, the mixture of reactive components, active liquid and optional liquids, while still uncured, may be dispersed in water or other aqueous medium and the resulting emulsion optionally stabilized by means of a surfactant. Droplets of inventive composition thus emulsified then may cure, resulting in a dispersion of solid gel particles. This may be considered a process for preparing encapsulated active oils in dispersed form. Such a material is a milky liquid and can, as such, be impregnated into a porous medium such as paper, cardboard, cellulose pad, cellulose pulp, felt, fabric, a porous synthetic foam, a porous ceramic, activated carbon, soil, diatomaceous earth, kieselguhr, sand, charcoal, silica, clay, and the like or coated onto a non-porous substrate included but not limited to plastic films, metallic foils, rubber, ceramics, wood, glass, and leather.

Another embodiment of the article of the invention is a container nearly filled with a volatile active liquid that is then filled up with and sealed by the inventive composition, trapping the volatile material behind a barrier or membrane of cross-linked matrix. Such an arrangement is advantageous since the reservoir of volatile liquid is then released very slowly and continuously as it diffuses through the barrier of liquid-impregnated matrix.

When the article of the present invention is an air freshener, it may be "active" and/or "passive". Active air fresheners encompass relatively complex devices having moving parts such as heaters and fans to dispense concentrated or diluted aroma compounds or spray cans charged with aroma chemical, carrier liquid, and propellant. Active air fresheners require the occupant to dispense the material into the area to be treated. Passive air fresheners are available in many forms, but are in essence "fixed" liquid chemicals: a multi-component article including fragrance oil immobilized in and/or a solid support. The support material can be simple, e.g. a piece of cardboard, blotter paper, cotton, or other fibrous materials. The support material can be complex, e.g. an aqueous dispersion (gelatin) or a non-aqueous gel (gelled, e.g. by polyamide resin). Preferably, the air fresheners of the present invention are transparent, but can be opaque.

The present invention is explained in more detail with the aid of the following embodiment examples that are not intended to limit the scope of the present invention in any manner.

EXAMPLES

Examples 1-4

Example 1

Air freshener components (names and amounts listed below) including a small amount of green dye, which were weighed into a glass vial and stirred together at ambient temperature by hand with a wooden stir stick. A portion of the mixture (8.0 g) was then poured into a flat, rectangular, 2.50 inch×3.25 inch uncoated polystyrene mold:
Epoxy Resin: EPALLOY® 5001, 10.00 g; 55.1%
Hardener: 1,3-BAC, 3.55 g; 19.6%
Fragrance Oil: Belle Aire "Evergreen", 4.55 g; 25.1%
Dye: Green, 0.05 g; 0.3%.

The next day the sample was firm, clear, tack-free, and flexible. It could be removed from the mold by hand with only a slight amount of sticking to the mold. Placed in a polyethylene "baggie" for storage at room temperature, it exhibited no syneresis, even after a number of weeks.

Example 2

These air freshener components totaling 100 parts by weight were treated following the procedure of Example 1: EPALLOY® 5001 (53.6 parts), 1,3-BAC (19.0 parts), Belle Aire "Evergreen" fragrance oil (25.1 parts), nonyl phenol (2.2 parts). The resulting article after curing at room temperature for one day was transparent, firm, flexible and tack-free.

Example 3

These air freshener components totaling 100 parts by weight were treated following the procedure of Example 1: Cyclohexane dimethanol diglycidyl ether (22.8 parts), EPON® 828 (22.8 parts), Huntsman T-403 polyamine (24.2 parts), Continental Aromatics "Country Meadow" fragrance oil (30.0 parts), plastic glitter 0.1 parts) and a trace of green dye. The resulting article after curing at room temperature for three days was transparent, firm, flexible, tack-free and exhibited ability to cling lightly to a flat vertical glass surface from which it could be easily removed and re-applied without marring the surface.

Example 4

A polyamide polyamine was prepared by charging adipic acid (20.0 g, 274 meq acid), JEFFAMINE® T-403 polyamine (20 g, 132 meq amine) and Huntsman XTJ-500 (80 g, 254 meq. amine) to a 250 mL glass flask equipped with a stirrer and heating this charge to 210-220° C. under a stream of dry nitrogen. After holding this mixture under these conditions for 5 hours, the reaction mixture was discharged to a container. The product was a clear, viscous, nearly water-white liquid having an acid number of 1.4, an amine number of 42.2, and a Brookfield viscosity at 150° C. of 340 cP. A portion of this product (11.63 g) was dissolved in water (27.5 g) and then blended with a polyethyleneglycol diglycidyl ether (EEW of 195; 3.40 g). To a portion of this mixture (20.0 g) in a small plastic jar with a screw cap was then added fragrance oil ("Sunshine Fruits", Firmenich fragrance oil #190196) and a few drops of Tween 80 surfactant, forming a milky emulsion which, after being capped and allowed to stand, gelled to an immobile firm homogeneous white solid that emitted the fragrance gradually after being un-capped.

Example 5

To a commercial resealable polyethylene "baggie" was added components totaling 100 parts by weight: cyclohexane dimethanol diglycidyl ether (13.9 parts), EPON® 826 (13.9 parts), Arizona proprietary liquid triethylenetetramine-based amido-amine #X54-327-004 (amine number of 349, acid number of 0.8, 22.2 parts), Atlas "Crisp Breeze" fragrance oil (50.0 parts), and a trace of blue dye. The "baggie" was massaged to blend the components for a few minutes, the air bubbles pressed out and the fluid mixture then stored lying flat at room temperature for one week. At that time the material was cross-linked to the point of being immobile, transparent, and flexible.

Example 6

To a glass beaker containing a magnetic stir bar was charged Huntsman Surfonic® L24-5, a liquid ethoxylated alcohol surfactant (12.0 g), Atlas Products "Crisp Breeze" fragrance oil (8.0 g), Huntsman T-403 polyamine (8.4 g), FD&C #3 blue-green dye (0.4 g) and HELOXY® 48 epoxy resin (14.0 g). This mixture was heated to 58° C. for about 3 hours with stirring to nearly cure it and then poured into a cylindrical mold and allowed to cool. After the material stood about three days at room temperature it was removed from the mold as a slightly rubbery, firm solid.

Example 7

These air freshener components totaling 100 parts by weight w ere blended at room temperature: cyclohexane dimethanol diglycidyl ether (25.3 parts), EPON® 828 (17.2 parts), Arizona proprietary polyamido-amine hardener #X54-327-004 (34.5 parts), Continental Aromatics "Ocean" fragrance oil (23.0 parts), and a trace of green dye. This blend was held for about 45 minutes at about 67° C., at which time it was allowed to cool to room temperature. It was, at this stage, quite viscous, but could still be poured and stirred. To this partially cross-linked intermediate was added with gentle distribution through the mass approximately two dozen ¼" colored foil hearts. The resulting article after curing at room temperature for three days was firm, flexible, and tack-free with the foil hearts clearly visible suspended uniformly inside it.

Example 8

These components totaling 100 parts by weight were treated following the procedure of Example 1: poly(propylene glycol)diglycidyl ether (13.0 parts), EPON® 828 (22.0 parts), Arizona UNI-REZ® 2801 amido-amine (14.0 parts), "Vanilla" fragrance oil from Aromatic Flavors and Fragrances, dipropyleneglycol benzoate (19.5 parts) and commercial ground coffee (29.5 parts). The resulting article after curing was firm, slightly flexible, non-tacky. The coffee grounds were uniformly distributed and gave the article a rich brown, opaque appearance, smooth at the bottom where the mold was smooth and rough on top where the grounds were allowed to settle freely.

In the following examples, abbreviations are as follows:
CHDA is 1, 4 cyclohexane dicarboxylic acid from Eastman Chemical;
Empol is EMPOL® 1008 dimer acid supplied by Cognis Corporation;
Unidyme is UNIDYME® 18 dimer acid supplied by Arizona Chemical Company;
T-403 is JEFFAMINE® T-403 poly(alkyleneoxy)diamine supplied by Huntsman Corporation;
D-400 is JEFFAMINE® D-400 poly(alkyleneoxy)diamine also from Huntsman;
D-2000 is JEFFAMINE®T-2000 poly(alkyleneoxy)diamine also from Huntsman;
V-551 is VERSAMINE® 551 dimer diamine supplied by Cognis Corporation;
N-3300 is DESMODUR® N-3300 or N-3300A, Bayer Corporation, Industrial Chemicals Division;
N-3800 is DESMODUR® N-3800, also from Bayer;
Z-4470 is DESMODUR® Z4470, also from Bayer.

Example 9

A polyamide polyamine was prepared by charging EMPOL® 1008 polymerized fatty acid (63.0 g, 219 meq acid), JEFFAMINE®T-403 polyamine (18 g, 118 meq amine) and JEFFAMINE® D-400 (45 g, 205 meq. amine) to a 250 mL glass flask equipped with a stirrer and heating this charge to 210-220° C. under a stream of dry nitrogen. After holding this mixture under these conditions for 5 hours, the reaction mixture was discharged to a container. The product was a clear, viscous, nearly water-white liquid having an acid number of 0.3, an amine number of 41.8, a weight average molecular weight of 2,270, and a Brookfield viscosity at 150° C. of 204 cP.

A solution was prepared by warming 10.0 g of this polyamide polyamine with 5.0 g FINSOLV® TN benzoate ester and 10.0 g fragrance oil ("Linen Fresh", Wessel Fragrances), cooled to room temperature and blended thoroughly with a mixture of DESMODUR® Z4470 and 5.1 g additional fragrance oil. To the composition was then added a small amount of red dye and red glitter. A few minutes later about 25 g of this final formulation was poured into a flat, circular rose-shaped silicone rubber mold and the remainder retained in a jar. A total of 33 minutes after the component were blended, the retained material was set to an immobile gel. After standing at room temperature for 16 hours, the immobilized fragrance oil article was removed from the mold. It did not adhere to the mold, was non-tacky, had the exact flower shape of the mold, exhibited a uniform color and distribution of glitter, and could be handled without breaking up. It also exhibited excellent cling to a variety of vertical surfaces including glass and plastic film.

Examples 10-15

Polyamide polyamines were prepared according to the procedure of Example 9 by charging acids and amines of the types listed in the TABLE A (below) in the weight percentages indicated to a reactor and heating the charge to 200-220° C. under a stream of dry nitrogen for about 4-5 hours and discharging the product. Products properties were then measured and are also recorded in TABLE A.

TABLE A

| Polyamide Polyamines Of Examples 10-15 | | | | | | |
|---|---|---|---|---|---|---|
| | EXAMPLE NUMBER | | | | | |
| | Example 10 | Example 11 | Example 12 | Example 13 | Example 14 | Example 15 |
| COMPONENTS | | | | | | |
| DiAcid | Adipic Acid | Empol | Empol | Empol | CHDA | Unidyme |
| Diamine | T-5000 | T-403 | T-403 | T-403 | T-403 | D-2000 |

TABLE A-continued

Polyamide Polyamines Of Examples 10-15

| | EXAMPLE NUMBER | | | | | |
|---|---|---|---|---|---|---|
| | Example 10 | Example 11 | Example 12 | Example 13 | Example 14 | Example 15 |
| Co-DiAmine | — | D-400 | D-400 | XTJ-500 | D-400 | Piperazine |
| Third Diamine | — | D-2000 | D-2000 | — | D-2000 | |
| COMPONENTS (Wt. %) | | | | | | |
| DiAcid | 2.0% | 41.2% | 30.8% | 43.3% | 18.7% | 82.3% |
| Diamine | 98.0% | 9.6% | 4.2% | 12.6% | 17.8% | 2.1% |
| Co-DiAmine | 0.0% | 24.6% | 16.7% | 44.1% | 35.5% | 15.6% |
| Third Diamine | 0.0% | 24.6% | 48.3% | 0.0% | 28.0% | 0.0% |
| PRODUCT PROPERTIES | | | | | | |
| Neutralization | 194.4% | 139.5% | 141.5% | 148.2% | 141.1% | 131.7% |
| Acid Number | 0.4 | 0.5 | 0.4 | 0.4 | 1.4 | 0.6 |
| Amine Number | 12.2 | 27.1 | 22.6 | 42.4 | 44.6 | 14.1 |
| Color | Pale yellow | Pale yellow | Pale yellow | Off-White | Pale yellow | Amber |
| Softening Point (R&B, ° C.) | Liquid | Liquid | Liquid | Liquid | 128 | Liquid |
| Viscosity At 150° C. | 770 | 391 | 141 | 190 | 290 | 481 |
| Wt. Aver. Mol. Wt. | 6,150 | 2,150 | 17,780 | 5,650 | 1,720 | 33,760 |

Immobilized fragrance oils were prepared by warming a mixture of 2.0 grams PAPA of the example and 2.0 grams fragrance oil to about 55° C. and then blending the warm mixture by hand with a stir stick. Test fragrances were: "Ocean" (Continental Aromatics), "Linen Fresh" (Wessel Fragrances), and "Cherry" (Aromatic Flavors and Fragrances). After blending, one equivalent of isocyanate hardener dissolved in an equal weight of oil was added with manual stirring, a stopwatch was started, and the mixture monitored for its consistency. When the mixture no longer could flow under its own weight, the time (in minutes) was noted as the "gel time". TABLE B shows that all of these polyamide polyamines were effective in immobilizing the target oils when cross-linked with polyisocyanates. Gel times were short but not so short as to preclude the preparation of useful articles and followed the consistant pattern: Ocean<Linen Fresh<<Cherry.

TABLE B

Gel Times of The Formulations of Examples 10-15
(Minutes at 50 Wt % Matrix)

| GEL COMPONENTS | | POLYAMIDE POLYAMINE OF EXAMPLE | | | | | | |
|---|---|---|---|---|---|---|---|---|
| Fragrance Oil Type | Hardener | No. 9 | No. 10 | No. 11 | No. 12 | No. 13 | No. 14 | No. 15 |
| Ocean | N-3300 | 6.5 | 15 | 10 | 40 | 8.5 | 10 | 73 |
| Linen Fresh | N-3300 | 9 | 24 | 13 | 55 | 10 | 13 | 76 |
| Linen Fresh | Z-4470 | 33* | 44 | 22 | nd | nd | nd | nd |
| Cherry | N-3300 | 75 | 170 | 95 | 335 | 87 | nd | nd |

*40% polyurea- see Example 9 for conditions

Examples 16-20

Polyamide polyamines (PAPA) were prepared according to the procedure of Ex. 9 by charging acids and amines of the types listed in the TABLE C in the weight percentages indicated to a reactor and heating the charge to 200-220° C. under a stream of dry nitrogen for about 5 hours and discharging the product. Products properties were then measured and are also recorded in TABLE C.

TABLE C

Polyamide Polyamines Of Examples 8-20

| | EXAMPLE | | | | |
|---|---|---|---|---|---|
| | No. 16 | No. 17 | No. 18 | No. 19 | No. 20 |
| COMPONENTS | | | | | |
| DiAcid | Empol | Adipic Acid | Adipic Acid | Empol 1008 | Unidyme |
| Triamine | T-403 | T-403 | T-403 | — | — |
| Diamine | D-400 | XTJ-500 | D-400 | D-400 | V-551 |
| Third Amine | D-2000 | — | D-2000 | D-2000 | — |
| WEIGHT % | | | | | |
| DiAcid | 30.6% | 18.2% | 15.2% | 36.7% | 41.7% |
| Triamine | 5.0% | 9.1% | 7.6% | — | — |
| Diamine | 16.5% | 72.7% | 38.6% | 22.9% | 58.3% |
| Third Amine | 47.9% | — | 38.6% | 40.4% | — |
| PROPERTIES | | | | | |
| Acid Number | 0.6 | 2.2 | 0.7 | 0.7 | 1.1 |
| Amine Number | 27.0 | 28.9 | 29.9 | 13.1 | 33.2 |
| Color | Colorless | Colorless | Colorless | Colorless | Amber |
| Viscosity [cP at 150° C.] | 106 | 393 | 198 | 1340 | 656 |
| Weight Aver. MW | 26380 | 12230 | 13490 | 31550 | 13180 |

Immobilized fragrance oils were prepared by warming a mixture of 2.0 grams polyamide polyamine of the example and 2.0 grams fragrance oil to about 55° C. and then blending the warm mixture by hand with a stir stick. Test fragrances were: Oceanside Mist, Tropical (Atlas Products), Spring Meadow, Country Wildflower, Ocean (Continental Aromatics), Linen Fresh (Wessel Fragrances), Yankee Home (Belle Aire), Mulberry and Cherry (Aromatic Flavors and Fragrances). After blending, one equivalent of isocyanate hardener dissolved in an equal weight of oil was added with manual stirring, a stopwatch was started, and the mixture monitored for its consistency. When the mixture no longer could flow under its own weight, the time (in minutes) was noted as the "gel time". TABLE D shows that all of these polyamide polyamines were effective in immobilizing the target oils when cross-linked with polyisocyanates. Gel times were short but not so short as to preclude the preparation of useful articles and followed the consistant pattern:
Spring Meadow<Ocean<Tropical<Linen Fresh<Yankee Home<Mulberry<Cherry

TABLE D

Gel Times of The Formulations of Examples 16-20
(Hardener is DESMODUR ® N3300A, minutes at 50 wt % polyurea)

| | Polyamide Polyamine of Example | | | | |
|---|---|---|---|---|---|
| Fragrance Oil Type | No. 16 | No. 17 | No. 18 | No. 19 | No. 20 |
| Oceanside Mist | Nd | nd | nd | 41 | nd |
| Spring Meadow | Nd | nd | nd | 42 | nd |
| Country Wildflower | Nd | nd | nd | 75 | nd |
| Ocean | 32 | 14 | 18 | >180 | 4 |
| Tropical | 38 | nd | 29 | >180 | nd |
| Linen Fresh | 40 | 20 | 32 | 225 | 13 |
| Yankee Home | 80 | 27 | 51 | >180 | nd |
| Mulberry | 315 | 185 | 250 | nd | nd |
| Cherry | >420 | 360 | >300 | >180 | 240 |

Example 21

A number of batches of a PAPA were prepared by the method of Example 9 using a charge (weight percentages in brackets) of either EMPOL® 1008 or UNIDYME® 12 (a low trimer content, hydrogenated dimer acid obtained from Arizona Chemical) [29.5%], T-403 [3.7%], D-400 [22.6%], and D-2000 [44.2%]. This polymer, used in Examples #22-35, typically had an amine number of 30-35 (equivalent wt. of 1,800-1,600), a weight-average molecular weight of 10,700-12,100, a number-average molecular weight of 4,300-4,900, and a viscosity at 150° C. of 40-70 cP.

Example 22

This example illustrates the preparation of an air freshener in a simple geometric shape. To a glass mixing jar was charged 13.1 g of Ex. 21 PAPA and 15 g of "Cotton Fresh" fragrance oil (Symrise Corp.) and the mixture was stirred gently for 15 minutes at ambient temperature. Blue dye (2 drops) was added to the mixture, turning the solution light blue. To this homogeneous mixture was then added 1.5 g of DESMODUR® N3300A. This mixture was then stirred until homogeneous, allowed to stand a few minutes to allow any air bubbles to dissipate, and 13 g total was poured into a rectangular-shaped flexible silicone mold of uniform length of 1.87 inches, height of 0.3 inches, and width of 1.0 inches. The set time was recorded at 28 minutes. The mixture was covered with polyethylene film and allowed to cure undisturbed for 24 hours. After this time the mold was striped away from the cross-linked air freshener object that was now firm, flexible, transparent and non-tacky to the touch.

Example 23

This example illustrates the preparation of an air freshener in a complex shape. To a glass mixing jar was charged 13.1 g of Ex. 21 polyamine and 15 g of "Snuggle Type" fragrance oil (Alpha Aromatics) and the mixture was stirred gently for 15 minutes at ambient temperature. Red dye (3 drops) was added to the mixture, turning the solution light pink/red. To this homogeneous mixture was then added 1.5 g of DESMODUR® N3300A. This mixture was then stirred briefly (until homogeneous), allowed to stand a few minutes to allow any air bubbles to dissipate, 10 g total was poured into a circular-shaped briochette flexible silicone mold of uniform top-width of 1.875 inches, height of 0.375 inches, and bottom-width of 1.625 inches. The set time was 6 minutes. The mixture was covered with polyethylene film and allowed to cure undisturbed for 24 hours. After this time the mold was striped away from the cross-linked air freshener article that was now firm, flexible, transparent and non-tacky to the touch.

Example 24

This example illustrates the preparation of an air freshener in a complex shape. To a glass mixing jar was charged 19 g of Ex. 21 polyamine and 20 g of "Tropical Splash" fragrance oil (obtained from Symrise Corp.) and the mixture was stirred gently for 15 minutes at ambient temperature. Blue dye (3 drops) was added to the mixture, turning the solution light green. To this homogeneous mixture was then added 2.0 g of DESMODUR® N3300A. This mixture was then stirred briefly (until homogeneous), allowed to stand a few minutes to allow any air bubbles to dissipate, 20 g total was poured into a scallop-shaped flexible silicone mold of uniform top-width of 2.375 inches, height of 0.125 inches, and bottom-width of 2.25 inches. The set time was recorded at 24 minutes. The mixture was covered and allowed to cure undisturbed for 24 hours. After this time the mold was striped away from the cross-linked air freshener article that was now firm, flexible, transparent and non-tacky to the touch

Example 25

This example illustrates the preparation of an air freshener containing suspended insoluble particles. To a glass mixing jar was charged 19 g of Ex. 21 polyamine and 20 g of "Clean Citrus" fragrance oil (from Symrise Corp.) and the mixture was stirred gently for 15 minutes at ambient temperature. Yellow aluminum flake "glitter" (0.04 g) was added to the mixture. To this homogeneous mixture was then added 2.0 g of DESMODUR® N3300A. This mixture was then stirred briefly (until homogeneous), allowed to stand a few minutes to allow any air bubbles to dissipate, 18.0 g total was poured into a disk-shaped flexible silicone mold of uniform circumference of 9.75 inches, height of 0.75 inches, and width of 3.0 inches. The set time was recorded at 30 minutes. The mixture was covered and allowed to cure undisturbed for 24 hours. After this time the mold was striped away from the cross-linked air freshener article that was now firm, flexible, transparent and non-tacky to the touch and displayed a uniform distribution of glitter.

Example 26

To a glass mixing jar was charged 19 g of Ex. 21 polyamine and 20 g of "Sunshine Fruit" fragrance oil (Firmenich, Inc.) and the mixture was stirred gently for 15 minutes at ambient temperature. Green "glitter" (0.03 g) was added to the mixture. To this homogeneous mixture was then added 2.0 g of DESMODUR® N3300A. This mixture was then stirred briefly (until homogeneous), allowed to stand a few minutes to allow any air bubbles to dissipate, 28.0 g total was poured into a heart-shaped flexible silicone mold of uniform length of 2.5 inches, height of 0.3 inches, and width of 2.875 inches. The set time was recorded at 17 minutes. The mixture was covered and allowed to cure undisturbed for 24 hours. After this time the mold was striped away from the cross-linked air freshener object that was now firm, flexible, transparent and non-tacky to the touch and displayed a uniform distribution of glitter.

Example 27

To a glass mixing jar was charged 19 g of Ex. 21 PAPA and 20 g of "Mandarin Grapefruit" fragrance oil (obtained from Givaudan Corp.) and the mixture was stirred gently for 15 minutes at ambient temperature. Blue dye (1 drop) was added to the mixture, turning the solution light yellow/green. To this homogeneous mixture was then added 2.0 g of DESMODUR® N3300A. This mixture was then stirred briefly (until homogeneous), allowed to stand a few minutes to allow any air bubbles to dissipate, 31.0 g total was poured into a bundt cake-shaped flexible silicone mold of uniform top-width of 1.75 inches, height of 0.75 inches, and bottom-width of 2.5 inches. The set time was recorded at 67 minutes. The mixture was covered and allowed to cure undisturbed for 24 hours. After this time the mold was striped away from the cross-linked air freshener object that was now firm, flexible, transparent and non-tacky to the touch.

Example 28

This example illustrates the preparation of an immobilized phase-transfer liquid. To a glass mixing jar was charged 10.4 g of Ex. 21 polyamine and 18 g of 1-decanol (freezing point, 5-7oC) as the active oil, 0.6 g benzaldehyde as odorant and cross-linking reaction retardant and the mixture was stirred gently for 15 minutes at ambient temperature. To this homogeneous mixture was then added 1.5 g of DESMODUR® N3300A. This mixture was then stirred briefly (until homogeneous), allowed to stand a few minutes to allow any air bubbles to dissipate and then 18.5 g total was poured into a truncated pyramid-shaped flexible silicone mold of uniform top-width of 0.75 inches, height of 0.75 inches, and bottom-width of 1.0 inches. The set time was recorded at 30 minutes. The mixture was covered and allowed to cure undisturbed for 24 hours. After this time the mold was striped away from the cross-linked object that was now firm, flexible, transparent and non-tacky to the touch. When placed in a freezer. The object hardened but did not crack. When removed from the freezer and allowed to warm to room temperature, the object regained flexibility but remained a tough, firm clear, solid.

Example 29

This example illustrates the preparation of a small air freshener for use in a purse or other small enclosed space): To a glass mixing jar was charged 5 g of Ex. 21 polyamine and 5 g of "Ocean" fragrance oil (provided by Orlandi, Inc.) and the mixture was stirred gently for 15 minutes at ambient temperature. Blue dye (2 drops) was added to the mixture, turning the solution light blue. To this homogeneous mixture was then added 0.6 g of DESMODUR® N3300A. This mixture was then stirred briefly (until homogeneous), allowed to stand a few minutes to allow any air bubbles to dissipate, 5.0 g total was poured into a lozenge-shape polyethylene bulb mold of uniform middle-circumference of 1.5 inches, height of 1.625 inches, and top and bottom-width of 0.5 inches. The set time was 7 minutes. The mixture was sealed and allowed to cure undisturbed for 24 hours. After this time the mold was striped away from the cross-linked air freshener object that was now firm, transparent and non-tacky to the touch.

Example 30

To a glass mixing jar was charged 28 g of Ex. 21 polyamine and 30 g of "Country Garden" fragrance oil (Belle-Aire) and the mixture was stirred gently for 15 minutes at ambient temperature. Green dye (3 drops) and yellow sprinkles (0.02 g) were added to the mixture, turning the solution yellow/green. To this homogeneous mixture was then added 3.0 g of DESMODUR® N3300A. This mixture was then stirred briefly (until homogeneous), allowed to stand a few minutes to allow any air bubbles to dissipate, 50.0 g total was poured into a Half sphere-shaped flexible silicone mold of bottom-circumference of 7.25 inches, height of 1.0 inches, and bottom-width of 3.75 inches. The set time was 260 minutes. The mixture was covered and allowed to cure undisturbed for 24 hours. After this time the mold was striped away from the cross-linked air freshener object that was now firm, flexible, transparent and non-tacky to the touch.

Example 31

To a glass mixing jar was charged 30 g of Ex. 21 polyamine and 30 g of "Cotton Fresh" fragrance oil (Symrise) and the mixture was stirred gently for 15 minutes at ambient temperature. Autumn leaves foil confetti (6 leaves) were added to the clear mixture. To this homogeneous mixture was then added 3.5 g of DESMODUR® N3300A. This mixture was then stirred briefly (until homogeneous), allowed to stand a few minutes to allow any air bubbles to dissipate, and 50 g total was poured into a glass jar of uniform circumference of 7.25 inches, height of 1.25 inches, and top and bottom-width of 2.25 inches. The set time was recorded at 28 minutes. The mixture was capped and allowed to cure undisturbed for 24 hours. After this time the mold was now firm, transparent and smooth to the touch.

Example 32

To a glass mixing jar was charged 37 g of Ex. 21 polyamine and 40 g of "Lemon Citrus" fragrance oil (Alpha Aromatics) and the mixture was stirred gently for 15 minutes at ambient temperature. Green sprinkles (0.02 g) were added to the mixture, turning the solution yellow/green. To this homogeneous mixture was then added 4.0 g of DESMODUR® N3300A. This mixture was then stirred briefly (until homogeneous), allowed to stand a few minutes to allow any air bubbles to dissipate, 60.0 g total was poured into a lemon-shaped flexible silicone mold of uniform top and bottom-width of 0.75 inches, height of 2.75 inches, and middle-circumference of 5.5 inches. The set time was recorded at 42 minutes. The mixture was covered and allowed to cure undisturbed for 24 hours. After this time the mold was striped away from the cross-linked air freshener object that was now film, flexible, transparent and non-tacky to the touch.

Example 33

To a glass mixing jar was charged 36 g of Ex. 21 polyamine and 40 g of "Cherry Berry" fragrance oil (Belle-Aire) and the mixture was stirred gently for 15 minutes at ambient temperature. Red dye (3 drops) was added to the mixture, turning the solution red. To this homogeneous mixture was then added 4.0 g of DESMODUR® N3300A. This mixture was then stirred until homogeneous, allowed to stand a few minutes to allow any air bubbles to dissipate, 60.0 g total was poured into a rose flower-shaped flexible silicone mold of uniform top and bottom-width of 3.75 inches, height of 0.75 inches, and circumference of 12.25 inches. The set time was recorded at 155 minutes. The mixture was covered and allowed to cure undisturbed for 24 hours. After this time the mold was striped away from the cross-linked air freshener object that was now firm, flexible, transparent and non-tacky to the touch.

Example 34

To a glass mixing jar was charged 19 g of Ex. 21 polyamine and 20 g of "Cherry" fragrance (Atlas, Inc.) and the mixture was stirred gently for 15 minutes at ambient temperature. Red dye (3 drops) was added to the mixture, turning the solution red. To this homogeneous mixture was then added 2.0 g of DESMODUR® N3300A. This mixture was then stirred briefly (until homogeneous), allowed to stand a few minutes to allow any air bubbles to dissipate, 28.0 g total was poured into a hollow polyethylene golf ball mold of uniform circumference 5.25 inches. The set time was recorded at 75 minutes. The mixture was covered and allowed to cure undisturbed for 24 hours. After this time the mold was striped away from the cross-linked air freshener object that was now firm, flexible, transparent and non-tacky to the touch.

Example 35

This example illustrates the preparation of a foamed article. To a glass mixing jar was charged 15 g of Ex. 21 polyamine, 15 g of UNIDYME® 60 polymerized fatty acid (from Arizona Chemical) and 30 g of "Very Berry" fragrance oil (from Belmay Corp.) and the mixture was stirred gently for 15 minutes at ambient temperature, resulting in a slightly hazy solution. Red dye (3 drops) was added to the mixture, turning the solution red. To this homogeneous mixture was then added 4.0 g of DESMODUR® N3300A. This mixture was then stirred briefly (until homogeneous), allowed to stand a few minutes to allow any air bubbles to dissipate, 40 g total was poured into a baking cup paper mold of uniform top and bottom-width of 2.0 inches, height of 1.25 inches, and circumference of 7.5 inches. The set time was 8 minutes. The mixture was allowed to cure undisturbed for an additional 24 hours. During this time the object became filled with trapped bubbles (foam) and doubled in size, forming a rounded crown. This foam air freshener was now firm and non-tacky to the touch. When compressed (squeezed), it returned to its rounded shape.

Example 36

A number of batches of a polyamide polyamine terminated with a carbonyl-substituted aromatic amine were prepared by charging (weight percentages in brackets) of PRIPOL®1009 hydrogenated dimer acid [24.0], para-aminobenzoic acid [5.0], JEFFAMINE® D-2000 [54.0], JEFFAMINE® D-400 [11.5], and JEFFAMINE® T-403[5.5] to a 3 L glass round-bottomed reactor equipped with an overhead mechanical stirrer and heating this charge to 215° C. under a stream of dry nitrogen. After holding this mixture under these conditions for about 25 hours, the reaction mixture was discharged to a container. The product was a clear, viscous, slightly yellow liquid. This polymer had a titrated amine number in the range 13-15 (non-potentiometric method, or 30-35 by potentiometric titration, amine reactive equivalent wt. of 1,800-1,600), a weight-average molecular weight of 13,000-14,000, a number-average molecular weight of 4,500-5,500, and a viscosity at 130° C. of 250 cP. This material was used in a series of tests of immobilizing, at the 30 weight % use level, liquid test media (70% by weight), free of active, catalyst, or retardant. The results (TABLE, below) demonstrate that set times can vary up to about 1 day for such a modified PAPA even in the absence of retardant aldehyde. The data also demonstrate the accelerating effect of the use of an alcoholic diluent, such as a polypropylene glycol or its alkyl ether, on the cure rate.

| Test Liquid Medium | Set Time (Minutes) | Upon Curing Appearance | Syneresis (after 4 days) |
| --- | --- | --- | --- |
| Dipropylene Glycol | 60 | Hazy | Slight syneresis |
| Isostearyl Alcohol | 60 | Hazy | No syneresis |
| Tripropylene Glycol | 66 | Slight Haze | Significant syneresis |
| Dipropylene Glycol Mono Methyl Ether | 90 | Clear | No syneresis |
| Castor Oil | 105 | Slight Haze | No syneresis |
| Methyl Salicylate | 400 | Clear | No syneresis |
| FINSOLV TN Benzoate Ester | 440 | Clear | No syneresis |
| Dibutyl Adipate | 1014 | Clear | No syneresis |
| Dipropylene Glycol Dimethyl Ether | 1245 | Clear | No syneresis |
| Diethyl-m-toluamide (DEET) | 1470 | Clear | No syneresis |
| Isophorone | 1845 | Clear, yellow | No syneresis |

Example 37

This example illustrates the preparation of another type of polyamide polyamine terminated with a carbonyl-substituted aromatic amine. The procedure of Example 37 was followed using a charge (weight percentages in brackets) of T-5000 [92.9] and para-aminobenzoic acid [7.1]. This polymer, used in Examples #38-41, had an amine equivalent weight of 1.950.

Example 38

This example illustrates the preparation of an article containing liquid fragrance trapped behind a membrane of matrix. To a glass mixing jar was charged 5.0 g of the Ex. 36 polyamine and 5.0 g of FINSOLV® TN and the mixture was stirred gently for 15 minutes at ambient temperature. To this homogeneous mixture was then added 0.6 g of DESMO-DUR® N3300A. This mixture was then stirred briefly (until homogeneous), allowed to stand a few minutes to allow air bubbles to dissipate, and then a 1.0 g portion was poured gently, without stirring, into a 1 oz. glass vial containing 10 g of "Lily of the Valley" green fragrance oil (Wellington Fragrances). The matrix solution floated on top of the fragrance oil and the oil remained as a separate reservoir below it. The set time for the top (membrane) layer that gradually absorbed some of the fragrance oil, was 80 minutes. The vial was capped and allowed to cure for an additional 24 hours. After this time, the vial was suspended inverted. In this position, fragrance oil gradually permeated the membrane and evaporated, acting as a sustained release air freshener.

Example 39

This example illustrates the preparation of a article containing an aromatic filler. To a glass mixing jar was charged 15 g of Ex. 36 polyamine, 6 g of castor oil, and 9 g of commercial ground coffee and the mixture was stirred gently for 30 minutes at ambient temperature. To this viscous paste was then added 2.0 g of DESMODUR® N3300A. This mixture was then stirred briefly, allowed to stand a few minutes to allow any air bubbles to dissipate, poured (18.0 g used) into a disk-shaped flexible mold of uniform circumference of 8.25 inches, height of 0.25 inches, and top and bottom-width of 2.5 inches. The set time was recorded at 165 minutes. The mixture was covered and allowed to cure undisturbed for 24 hours. After this time the mold was striped away from the object that was now fragrant (coffe odor), firm, flexible, and non-tacky to the touch.

Example 40

This example illustrates the preparation of an article containing water. To a glass mixing jar was charged 20 g of Ex. 36 polyamine, 20 g of "Snuggle Type" fragrance oil (from Alpha Aromatics), and 8 g of de-ionized water, and the mixture was stirred gently for 15 minutes at ambient temperature, resulting in a milky suspension of water in the matrix-fragrance solution. Blue dye (2 drops) was added to the mixture. To this light blue, milky mixture was then added 2.5 g of DESMO-DUR® N3300A. This mixture was then stirred briefly and allowed to stand a few minutes to allow any air bubbles to dissipate. Then a 31.0 g portion was poured into a bunt cake-shaped flexible silicone mold of uniform top-width of 1.75 inches, height of 0.75 inches, and bottom-width of 2.5 inches. The set time was recorded at 130 minutes. The mixture was covered and allowed to cure undisturbed for 24 hours. After this time the mold was striped away from the cross-linked air freshener object that was now firm, milky, flexible, and non-tacky to the touch. The article gradually turned clear (starting from the edges and moving toward the center) as the water evaporated over a period of one month.

Example 41

This example illustrates the preparation of a dispersion. Solution A: to a glass mixing jar was charged 8 g of the Ex. 36 polyamine and 8 g of FINSOLV® TN and the mixture was stirred gently for 15 minutes at ambient temperature. To this homogeneous mixture was then added 0.8 g of DESMO-DUR® N3300A. This mixture was then stirred briefly (until homogeneous), allowed to stand a few minutes to allow any air bubbles to dissipate. Solution B: to another glass mixing jar was charged 32 g deionized water and 0.8 g of surfactant (T-DET A-136). This mixture was stirred (10 minutes). Solution A was then poured into Solution B with stirring for 10 minutes. This blend of mixture A+B mixture was then poured into a metal pan and the water allowed to evaporate (24 hours). This yielded a white, lubricious powder, insoluble in toluene, of immobilized oil particles.

Example 42

Representative of articles containing pesticide that can be prepared according to the present invention is the following controlled-release diethyl toluamide (DEET) device. A thorough mixture was made of DEET (20 parts), dimethyl adipate carrier (50 parts), benzaldehyde as fragrance and retardant (1.6 parts), the polyamide polyamine of Example 21 (26.8 parts) and a trace of orange dye. To this blend was then added with stirring DESMODUR® N3300 polyisocyanate (3.2 parts) and the final mixture poured into scallop-shaped silicone molds. After this cured, the scallop medallion so formed was a firm, non-tacky, and flexible solid.

Example 43

Representative of articles containing pheromones that can be prepared according to the present invention is the following controlled-release device for the pheromone octadecanal. A thorough mixture was made of octadecanal (30 parts), FINSOLV® TN benzoate ester as carrier (30 parts), and the polyamide polyamine of Example 21 (35.5 parts). To this blend was then added with stirring DESMODUR® N3300 polyisocyanate (4.5 parts) and the final mixture poured into a cylindrical mold. After curing, the material formed was a firm, non-tacky, and flexible solid that could be sliced into small disks for use as lures.

Example 44

This example illustrates the use of a styrene-maleic anhydride copolymer as the reactive partner with a polyamide polyamine for preparation of a lightly-scented disk-shaped air freshener. To a glass mixing vial was charged 6.0 g of a 25 wt % solution FINSOLV® TN solution of Ex. 21 polyamide polyamine, 7.5 g of a 20 wt % solution of DYLARK® 232 poly(styrene-co-maleic anhydride, NOVA Chemicals), and ca. 2 g of "Ocean" fragrance oil (provided by Wellington, Inc.). The mixture was stirred gently for a few minutes at ambient temperature and blue dye (4 drops) added. The mixture was initially slightly turbid but cleared after a few more minutes and remained clear and apparently homogeneous. The mixture was then poured (about 11 g was used) into a disk-shaped polyethylene mold and allowed to stand undisturbed. The mixture set to a sticky, elastic mass inside about 2 hours and after 24 hours could be stripped from the mold. After this time the mold was striped away from the cross-linked air freshener object that was now firm, transparent and flexible with a light tack to the touch.

Example 45

This example illustrates the use of a cationic surfactant to prepare an immobilized fragrance emulsion useful as a fabric softener. A blend of PAPA of Example 13 (4.0 g), "Cinnamon Chai" fragrance oil (3.0 g), and VARIQUAT® B 1216 alkyl dimethyl benzyl ammonium chloride (80% active, Degussa Corporation, 1.0 g) was first prepared by warming and stirring the ingredients. To the blend was added water (9.0 g) and then, with stirring, DESMODUR® N3300A (0.65 g). The mixture soon became viscous and uniformly cloudy. It was storage stable and was dilutable with water, indicating it was an oil-in-water dispersion. Light scattering particle size measurement on the material determined the particle size distribution to be bi-modal, with about 50% of the weight of particles having a size grouping around 0.4 microns and the other 50% grouping around 3.0 microns.

Example 46

This example illustrates the preparation of an immobilized cationic surfactant useful as a fabric softener. A blend of PAPA of Example 21 (3.0 g), DOWANOL® DPM (1.0 g) and VARIQUAT® B1216 alkyl dimethyl benzyl ammonium chloride (80% active, Degussa Corporation, 6.0 g) was first prepared by warming and stirring the ingredients and then cooling them to room temperature. A second blend was prepared of DOWANOL® DPM (4.2 g) and DESMODUR® N3300A (0.8 g). The two clear mixtures were then mixed together and immediately poured into a mold. The blended components set almost immediately and were firm enough to pick up out of the mold in less than 30 minutes. The final article contained 32% by weight active quaternary compound.

As used throughout, ranges are used as a short hand for describing each and every value that is within the range, including all subranges therein.

Numerous modifications and variations on the present invention are possible in light of the above teachings. It is, therefore, to be understood that within the scope of the accompanying claims, the invention may be practiced otherwise than as specifically described herein.

All of the references, as well as their cited references, cited herein are hereby incorporated by reference with respect to relative portions related to the subject matter of the present invention and all of its embodiments.

The invention claimed is:

1. An article comprising a porous support material and a composition disposed therein, the composition comprising a cured polymeric matrix and an active liquid, wherein said active liquid is immobilized throughout the cured polymeric matrix and the cured polymeric matrix is the reaction product of a compound having at least two isocyanate functional groups with a polyamine in the presence of said active liquid, wherein the polyamine includes a polyamide polyamine (PAPA) having a polyamide backbone comprising repeating monomer units terminated by amine groups that are not part of the monomer unit which is formed by the reaction of a polyacid with a stoichiometric excess of a polyamine.

2. The article of claim 1, wherein the porous support material comprises at least one selected from the group consisting of paper, cardboard, cellulose pad, cellulose pulp, felt, fabric, a porous synthetic foam, a porous ceramic, activated carbon, soil, diatomaceous earth, kieselguhr, charcoal, silica and clay.

3. The article of claim 2, wherein the article is selected from the group consisting of a therapeutic article having an active liquid that is therapeutic, a nutraceutical article having an active liquid that is nutritious, a pesticide article having an active liquid that is pesticidal, a laundry care article having an active liquid for laundry care, and an air freshener having an active liquid that is a fragrance oil.

4. The article according to claim 3, wherein the cured polymeric matrix is a reaction product of a compound having at least two isocyanate functional groups with a polyamine in the presence of the active liquid and a reaction accelerator.

5. The article according to claim 3, wherein the cured polymeric matrix is a reaction product of a compound having at least two isocyanate functional groups with a polyamine in the presence of the active liquid and a reaction retardant.

6. The article according to claim 3, wherein the reactive amine groups of the polyamine comprise amino groups derived from at least one of ortho-aminobenzoic acid or para-aminobenzoic acid.

7. The article according to claim 3, wherein the cured polymeric matrix is a reaction product of a compound having at least two non-aromatic isocyanate functional groups, which may be the same or different, with a polyamine in the presence of the active liquid.

8. The article according to claim 3, wherein the cured polymeric matrix is a reaction product of a compound having at least two isocyanate functional groups with a polyamine in the presence of the active liquid and wherein the polyamine has an amine number of from 10 to 100 meq KOH/g and has a viscosity, measured at 150° C., of no greater than about 500 cP.

9. The article according to claim 3, wherein the cured polymeric matrix is a reaction product of a compound having at least two isocyanate functional groups with a polyamine in the presence of the active liquid and wherein the polyamine is a liquid at room temperature.

10. An article comprising a part, component or member comprising a cured polymeric matrix and an active liquid, wherein said active liquid is immobilized throughout the cured polymeric matrix and the cured polymeric matrix is a reaction product of a compound having at least two isocyanate functional groups with a polyamine in the presence of said active liquid, wherein the polyamine includes a polyamide polyamine (PAPA) having a polyamide backbone comprising repeating monomer units terminated by amine groups that are not part of the monomer unit which is formed by the reaction of a polyacid with a stoichiometric excess of a polyamine.

11. The article of claim 10, wherein the article is selected from the group consisting of a therapeutic article having an active liquid that is therapeutic, a nutraceutical article having an active liquid that is nutritious, a pesticide article having an active liquid that is pesticidal, a laundry care article having an active liquid for laundry care, and an air freshener having an active liquid that is a fragrance oil.

12. The article according to claim 11, wherein the cured polymeric matrix is a reaction product of a compound having at least two isocyanate functional groups with a polyamine in the presence of the active liquid and a reaction retardant.

13. The article according to claim 11 wherein the reactive amine groups of the polyamine comprise amino groups derived from at least one of ortho-aminobenzoic acid or para-aminobenzoic acid.

14. The article according to claim 11 wherein the cured polymeric matrix is a reaction product of a compound having at least two non-aromatic isocyanate functional groups with a polyamine in the presence of the active liquid.

15. The article according to claim 11, wherein the article comprises a shape selected from the group consisting of triangular, square, circular, spherical, oval, regular geometric shapes, and irregular geometric shapes.

16. The article according to claim 11, wherein the cured polymeric matrix is a reaction product of a compound having at least two isocyanate functional groups with a polyamine in the presence of the active liquid and wherein the polyamine has an amine number of from 10 to 100 meq KOH/g and has a viscosity, measured at 150° C., of no greater than about 500 cP.

17. The article according to claim 11, wherein the cured polymeric matrix is a reaction product of a compound having at least two isocyanate functional groups with a polyamine in the presence of the active liquid and wherein the polyamine is a liquid at room temperature.

18. An article comprising a support member and a solid composition supported thereon, the solid composition comprising a cured polymeric matrix and an active liquid wherein said active liquid is immobilized throughout the cured polymeric matrix and the cured polymeric matrix is a reaction product of a compound having at least two isocyanate functional groups with a polyamine in the presence of said active liquid, wherein the polyamine includes a polyamide polyamine (PAPA) having a polyamide backbone comprising repeating monomer units terminated by amine groups that are not part of the monomer unit which is formed by the reaction of a polyacid with a stoichiometric excess of a polyamine.

19. The article of claim 18, wherein the article is selected from the group consisting of a active liquid that is nutritious, a pesticide article having an active liquid that is pesticidal, a laundry care article having an active liquid for laundry care, and an air freshener having an active liquid that is a fragrance oil.

20. The article according to claim 18, wherein the cured polymeric matrix is a reaction product of a compound having at least two isocyanate functional groups with a polyamine in the presence of the active liquid and a reaction accelerator.

21. The article according to claim 18, wherein the cured polymeric matrix is a reaction product of a compound having at least two isocyanate functional groups with a polyamine in the presence of the active liquid and a reaction retardant.

22. The article according to claim 18, wherein the reactive amine groups of the polyamine comprise amino groups derived from at least one of ortho-aminobenzoic acid or para-aminobenzoic acid.

23. The article according to claim 18, wherein the cured polymeric matrix is a reaction product of a compound having at least two non-aromatic functional isocyanate groups selected from the group with a polyamine in the presence of the active liquid.

24. The article according to claim 18, wherein the article comprises a shape selected from the group consisting of triangular, square, circular, spherical, oval, regular geometric shapes, and irregular geometric shapes.

25. The article according to claim 18, wherein the support member comprises at least one selected from the group consisting of glass, ceramic, metal, paper, plastic, and an oil-impermeable material.

26. The article according to claim 18, wherein the cured polymeric matrix is a reaction product of a compound having at least two isocyanate functional groups with a polyamine in the presence of the active liquid and wherein the polyamine has an amine number of from 10 to 100 meq KOH/g and has a viscosity, measured at 150° C., of no greater than about 500 cP.

27. The article according to claim 18, wherein the cured polymeric matrix is a reaction product of a compound having at least two isocyanate functional groups with a polyamine in the presence of the active liquid and wherein the polyamine is a liquid at room temperature.

* * * * *